United States Patent
Wipf et al.

(10) Patent No.: US 10,968,196 B2
(45) Date of Patent: *Apr. 6, 2021

(54) SUBSTITUTED β-LAPACHONES FOR TREATING CANCER

(71) Applicant: University of Pittsburgh—Of the Commonwealth System of Higher Education, Pittsburgh, PA (US)

(72) Inventors: Peter Wipf, Pittsburgh, PA (US); Chaemin Lim, Pittsburgh, PA (US); Wei Qian, Pittsburgh, PA (US); Bennett Van Houten, Pittsburgh, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/599,339

(22) Filed: Oct. 11, 2019

(65) Prior Publication Data

US 2020/0095220 A1    Mar. 26, 2020

Related U.S. Application Data

(63) Continuation of application No. 15/580,416, filed as application No. PCT/US2016/036440 on Jun. 8, 2016, now Pat. No. 10,450,289.

(60) Provisional application No. 62/172,422, filed on Jun. 8, 2015.

(51) Int. Cl.
| | |
|---|---|
| A61K 31/352 | (2006.01) |
| C07D 311/92 | (2006.01) |
| A61K 45/06 | (2006.01) |
| A61P 25/28 | (2006.01) |
| A61P 35/00 | (2006.01) |
| C07D 405/12 | (2006.01) |

(52) U.S. Cl.
CPC ............ *C07D 311/92* (2013.01); *A61K 45/06* (2013.01); *A61P 25/28* (2018.01); *A61P 35/00* (2018.01); *C07D 405/12* (2013.01)

(58) Field of Classification Search
CPC ............................. A61K 31/352; C07D 311/92
USPC .......................................... 514/454; 549/389
See application file for complete search history.

(56) References Cited

U.S. PATENT DOCUMENTS

| | | | |
|---|---|---|---|
| 5,763,625 | A | 6/1998 | Boothman et al. |
| 5,824,700 | A | 10/1998 | Frydman et al. |
| 5,969,163 | A | 10/1999 | Frydman et al. |
| 7,528,174 | B2 | 5/2009 | Wipf et al. |
| 7,718,603 | B1 | 5/2010 | Wipf et al. |
| 7,790,765 | B2 | 9/2010 | Bartis et al. |
| 8,068,459 | B2 | 11/2011 | Kravtsov et al. |
| 9,006,186 | B2 | 4/2015 | Wipf et al. |
| 2007/0161544 | A1 | 7/2007 | Wipf et al. |
| 2007/0161753 | A1 | 7/2007 | Seo |
| 2009/0028952 | A1 | 1/2009 | Bartis et al. |
| 2014/0018317 | A1 | 1/2014 | Wipf et al. |
| 2016/0022825 | A1 | 1/2016 | Dhar et al. |

FOREIGN PATENT DOCUMENTS

| | | |
|---|---|---|
| WO | 2010009327 A1 | 1/2010 |
| WO | 2010009405 A2 | 1/2010 |
| WO | 2012112851 A2 | 8/2012 |
| WO | 2013123298 A1 | 8/2013 |

OTHER PUBLICATIONS

Park et al., "β-Lapachone induces programmed necrosis through the RIP1-PARP-AIF-dependent pathway in human hepatocellular carcinoma SK-Hep1 cells," Cell Death and Disease, 2014, pp. 1-10, vol. 5.
Pathak et al., "Mito-DCA: A Mitochondria Targeted Molecular Scaffold for Efficacious Delivery of Metabolic Modulator Dichloroacetate," ACS Chemical Biology, 2014, pp. 1178-1187, vol. 9.
Pink et al., "NAD(P)H:Quinone Oxidoreductase Activity is the Principal Determinant of β-Lapachone Cytotoxicity," The Journal of Biological Chemistry, 2000, pp. 5416-5424, vol. 275:8.
Planchon et al., "β-Lapachone-mediated Apoptosis in Human Promyelocytic Leukemia (HL-60) and Human Prostate Cancer Cells: A p53-independent Response," Cancer Res., 1995, pp. 3706-3711, vol. 55:17.
Qian et al., "Alterations in bioenergetics due to changes in mitochondrial DNA copy number," Methods, 2010, pp. 452-457, vol. 51.
Ray et al., "Reactive oxygen species (ROS) homeostasis and redox regulation in cellular signaling," Cellular Signalling, 2012, pp. 981-990, vol. 24.
Sabharwal et al., "Mitochondrial ROS in cancer: initiators, amplifiers or an Achilles' heel?" Nat. Rev. Cancer, 2014, pp. 709-721, vol. 14:11.

(Continued)

*Primary Examiner* — Douglas M Willis
(74) *Attorney, Agent, or Firm* — The Webb Law Firm

(57) ABSTRACT

Compounds are provided that are useful in treating cancer and neurodegeneration. The compounds comprise a β-lapachone or β-lapachone derivative tricyclic ortho-naphthoquinone moiety linked to a mitochondria-targeting moiety, for example as defined with respect to Formula (I):

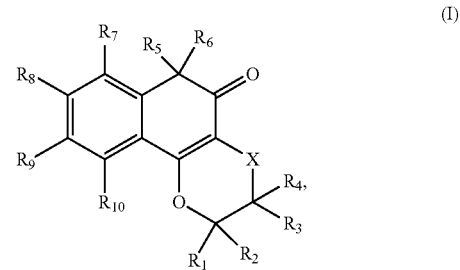

or a pharmaceutically-acceptable salt thereof. Pharmaceutical compositions are provided comprising the composition. Methods of treatment of cancer and neurodegenerative disorders also are provided.

20 Claims, 13 Drawing Sheets

(56) References Cited

OTHER PUBLICATIONS

Salas et al., "Trypanosoma cruzi: Activities of lapachol and a- and β-lapachone derivatives against epimastigote and trypomastigote forms," Bioorganic & Medicinal Chemistry, 2008, pp. 668-674, vol. 16.
Scherz-Shouval et al., "Regulation of autophagy by ROS: physiology and pathology," Trends in Biochemical Sciences, 2011, pp. 30-38, vol. 36:1.
Sena et al., "Physiological Roles of Mitochondrial Reactive Oxygen Species," Molecular Cell, 2012, pp. 158-167, vol. 48.
Sharma et al., "Mitochondrial Alteration: A Major Player in Carcinogenesis," Cell Biology, 2015, pp. 8-16, vol. 3:2-1.
Skoda et al., "Allylic Amines as Key Building Blocks in the Synthesis of (E)-Alkene Peptide Isosteres," Org Process Res Dev., 2012, pp. 26-34, vol. 16:1.
Sullivan et al., "Mitochondrial reactive oxygen species and cancer," Sullivan and Chandel Cancer & Metabolism, 2014, pp. 1-12, vol. 2:17.
Sun et al., "A Preparative Synthesis of Lapachol and Related Naphthoquinones," Tetrahedron Letters, 1998, pp. 8221-8224, vol. 39.
Tomasetti et al., "Redox-active and Redox-silent Compounds: Synergistic Therapeutics in Cancer," Current Medicinal Chemistry, 2015, pp. 552-568, vol. 22.
Trachootham et al., "Targeting cancer cells by ROS-mediated mechanisms: a radical therapeutic approach?" Nature Reviews Drug Discovery, 2009, pp. 579-591, vol. 8.
Uttara et al., "Oxidative Stress and Neurodegenerative Diseases: A Review of Upstream and Downstream Antioxidant Therapeutic Options," Current Neuropharmacology, 2009, pp. 65-74, vol. 7.
Wallace, "Mitochondria and cancer," Nat Rev Cancer, 2012, pp. 685-698, vol. 12:10.
Wang et al., "Activation of the NRF2 Signaling Pathway by Copper-Mediated Redox Cycling of Para- and Ortho-Hydroquinones," Chemistry & Biology, 2010, pp. 75-85, vol. 17.
Weinberg et al., "Targeting mitochondria metabolism for cancer therapy," Nat Chem Biol, 2015, pp. 9-15, vol. 11:1.
Wellington, "Understanding cancer and the anticancer activities of naphthoquinones—a review," RSC Advances, 2015, pp. 20309-20338, vol. 5.
Wipf et al., "Mitochondrial Targeting of Selective Electron Scavengers: Synthesis and Biological Analysis of Hemigramicidin-TEMPO Conjugates," J. Am. Chem. Soc., 2004, pp. 12460-12461, vol. 127.
Wipf et al., "Imine Additions of Internal Alkynes for the Synthesis of Trisubstituted (E)-Alkene and Cyclopropane Peptide Isosteres," Adv. Synth. Catal., 2005, pp. 1605-1613, vol. 347.
Wipf et al., "Three-Component Synthesis of a, β-Cyclopropyl-γ-Amino Acids," Organic Letters, 2005, pp. 1137-1140, vol. 7:6.
Wondrak, "Redox-Directed Cancer Therapeutics: Molecular Mechanisms and Opportunities," Antioxidants & Redox Signaling, 2009, pp. 3013-3069, vol. 11:12.
Wu et al., "Metabolic Reprogramming of Human Cells in Response to Oxidative Stress: Implications in the Pathophysiology and Therapy of Mitochondrial Diseases," Current Pharmaceutical Design, 2014, pp. 5510-5526, vol. 20.
Xun et al., "Targeting of XJB-5-131 to mitochondria suppresses oxidative DNA damage and motor decline in a mouse model of Huntington's disease," Cell Rep., 2012, pp. 1137-1142, vol. 2:5.
Yousif et al., "Mitochondria-Penetrating Peptides: Sequence Effects and Model Cargo Transport," ChemBioChem, 2009, pp. 2081-2088, vol. 10.
Yousif et al., "Targeting Mitochondria with Organelle-Specific Compounds: Strategies and Applications," ChemBioChem, 2009, pp. 1939-1950, vol. 10.
Zhang et al., "Induction of mitochondrial dysfunction as a strategy for targeting tumour cells in metabolically compromised microenvironments," Nature Communications, 2014, pp. 1-14, vol. 5:3295.
Zhao et al., "Cell-permeable Peptide Antioxidants Targeted to Inner Mitochondrial Membrane inhibit Mitochondrial Swelling, Oxidative Cell Death, and Reperfusion Injury," The Journal of Biological Chemistry, 2004, pp. 34682-34690, vol. 279:33.
Zhou et al., "Design of iron chelators with therapeutic application," Dalton Transactions, 2012, pp. 6371-6389, vol. 41.
Adam et al., "The HSP70 Modulator MAL3-101 Inhibits Merkel Cell Carcinoma," PLoS One, 2014, pp. 1-8, vol. 9.
Adam-Vizi et al., "Bioenergetics and the formation of mitochondrial reactive oxygen species," ScienceDirect, 2006, pp. 639-645, vol. 27:12.
Apostolova et al., "Molecular Strategies for Targeting Antioxidants to Mitochondria: Therapeutic Implications," Antioxidants & Redox Signaling, 2015, pp. 686-729, vol. 22:18.
Barnham et al., "Neurodegenerative Diseases and Oxidative Stress," Nature Reviews Drug Discovery, 2004, pp. 205-214, vol. 3.
Bey et al., "An NQO1- and PARP-1-mediated cell death pathway induced in non-small-cell lung cancer cells by b-lapachone," PNAS, 2007, pp. 11832-11837, vol. 104:28.
Bey et al., "Catalase Abrogates b-Lapachone—Induced PARP1 Hyperactivation—Directed Programmed Necrosis in NQO1-Positive Breast Cancers," Molecular Cancer Therapeutics, 2013, pp. 2110-2121, vol. 12:10.
Biasutto et al., "Mitochondrially targeted anti-cancer agents," Mitochondrian, 2010, pp. 670-681, vol. 10.
Brieger et al., "Reactive oxygen species: from health to disease," Swiss Medical Weekly, 2012, pp. 1-14, issue 142.
Chamberlain et al., "Targeted Delivery of Doxorubicin to Mitochondria," ACS Chemical Biology, 2013, pp. 1389-1395, vol. 8.
Chen et al., "Oxidative stress in neurodegenerative diseases," Neural Regeneration Research, 2012, pp. 376-385, vol. 7:5.
Costantini et al., "Mitochondrion as a Novel Target of Anticancer Chemotherapy," Journal of the National Cancer Institute, 2000, pp. 1042-1053, vol. 92:13.
Dörwald, "Side reactions in organic synthesis: A guide to successful synthesis design," Weinheim, 2005, Wiley-VCH Verlag GmbH & Co, KGaA, Preface.
Fink et al., "Hemigramicidin-TEMPO conjugates: Novel mitochondria-targeted Antioxidants," Crit, Care. Med, 2007, pp. S461-S467, vol. 35:9.
Frantz et al., "Mitochondria as a target in treatment," National Institute of Health Environ. Mol. Mutagen, 2010, pp. 462-475, vol. 11:25.
Frantz et al., "Synthesis of analogs of the radiation mitigator JP4-039 and visualization of BODIPY derivatives in mitochondria," National Institute of Health Orig. Biomol. Chem., 2013, pp. 4147-4153, vol. 51:5.
Fulda et al., "Targeting mitochondria for cancer therapy," Nature Reviews Drug Discovery, 2010, pp. 447-464, vol. 9.
Gorrini et al., "Modulation of oxidative stress as an anticancer strategy," Nature Reviews Drug Discovery, 2013, pp. 931-947, vol. 12.
Graves et al., "Point Mutations in c-Myc Uncouple Neoplastic Transformation from Multiple Other Phenotypes in Rat Fibroblasts," PLoS One, 2010, pp. 1-10, vol. 5:10.
Graves et al., "Mitochondrial Structure, Function and Dynamics Are Temporally Controlled by c-Myc," PLoS One, 2012, pp. 1-13, vol. 7:5.
Gruber et al., "Mitochondria-targeted antioxidants and metabolic modulators as pharmacological interventions to slow aging," Biotechnology Advances, 2013, pp. 563-592, vol. 3.
Hail et al., "Cancer chemoprevention and mitochondria: Targeting apoptosis in transformed cells via the disruption of mitochondrial bioenergetics/redox state," Mol. Nutr. Food Res., 2009, pp. 49-67, vol. 53.
Ho et al., "Importance of glycolysis and oxidative phosphorylation in advanced melanoma," Molecular Cancer, 2012, pp. 1-13, vol. 11:76.
Hoye et al., "Targeting Mitochondria," Accounts of Chemical Research, 2008, pp. 87-97, vol. 41:1.
Huang et al., "Superoxide dismutase as a target for the selective killing of cancer cells," Nature, 2000, pp. 390-395, vol. 407.

(56) References Cited

OTHER PUBLICATIONS

Jean et al., "Molecular Vehicles for Mitochondrial Chemical Biology and Drug Delivery," ACS Chemical Biology, 2014, pp. 323-333, vol. 9.
Ji et al., "Global lipidomics identifies cardiolipin oxidation as a mitochondrial target for redox therapy of acute brain injury," Nat. Neurosci., 2012, pp. 1407-1413, vol. 15:10.
Ji et al., "Deciphering of mitochondrial cardiolipin oxidative signaling in cerebral ischemia-reperfusion," Journal of Cerebral Blood Flow & Metabolism, 2015, pp. 319-328, vol. 35.
Jiang et al., "Structural Requirements for Optimized Delivery, Inhibition of Oxidative Stress, and Antiapoptotic Activity of Targeted Nitroxides," The Journal of Pharmacology and Experimental Therapeutics, 2007, pp. 1050-1060, vol. 320:3.
Jordan, "Tamoxifen: a most unlikely pioneering medicine," Nature Reviews Drug Discovery, 2003, pp. 205-213, vol. 2:3.
Kamata et al., "Topical Review Redox Regulation of Cellular Signaling," Cell. Signal., 1999, pp. 1-14, vol. 11:1.
Kanai et al., "Mitochondria targeting of radioprotectants using peptidyl conjugates," Org Biomol Chem., 2007, pp. 1-8, vol. 5:2.
Keinan et al., "Computational design, synthesis and biological evaluation of para-quinone-based inhibitors for redox regulation of the dualspecificity phosphatase Cdc25B," Org Biomol Chem., 2008, pp. 3256-3263, vol. 6:18.
Kung et al., "The Chemotheraputic Effects of Lapacho Tree Extract: β-Lapachone," Chemotherapy, 2014, pp. 1-5, vol. 3:2.
Li et al., "Release of Mitochondrial Cytochrome C in Both Apoptosis and Necrosis Induced by β-Lapachone in Human Carcinoma Cells," Molecular Medicine, 1999, pp. 232-239, vol. 5.
Li et al., "Potent Induction of Apoptosis by β-Lapachone in Human Multiple Myeloma Cell Lines and Patient Cells," Molecular Medicine, 2000, pp. 1008-1015, vol. 6:12.
Li et al., "Mechanistic studies of cancer cell mitochondria- and NQO1-mediated redox activation of beta-lapachone, a potentially novel anticancer agent," Toxicology and Applied Pharmacology, 2014, pp. 285-293, vol. 281.
Lin et al., "Mitochondrial dysfunction and oxidative stress in neurodegenerative diseases," Nature, 2006, pp. 787-795, vol. 443.
Ma et al., "Mitochondrial targeted b-lapachone induces mitochondrial dysfunction and catastrophic vacuolization in cancer cells," Bioorganic & Medicinal Chemistry Letters, 2015, pp. 4828-4833, vol. 25.
Modica-Napolitano et al., "Mitochondrial dysfunction in cancer," Mitochondrion, 2004, pp. 755-762, vol. 4.
Munoz-Pinedo et al., "Autosis: a new addition to the cell death tower of babel," Cell Death and Disease, 2014, pp. 1-2, vol. 5.
Murphy et al., "How mitochondria produce reactive oxygen species," Biochem. J., 2009, pp. 1-13, vol. 417.
Murphy et al., "Targeting Antioxidants to Mitochondria by Conjugation to Lipophilic Cations," The Annual Review of Pharmacology and Toxicology, 2007, pp. 629-656, vol. 47.
Nakajima et al., "Metabolic Symbiosis in Cancer: Refocusing the Warburg Lens," Molecular Carcinogenesis, 2013, pp. 329-337, vol. 52.
Nakajima et al., "Quantifying Metabolic Heterogeneity in Head and Neck Tumors in Real Time: 2-DG Uptake is Highest in Hypoxic Tumor Regions," PLoS One, 2014, pp. 1-12, vol. 9:8.
Neuzil et al., "Classification of mitocans, anti-cancer drugs acting on mitochondria," Mitochondrion, 2013, pp. 199-208, vol. 13.
Newmeyer et al., "Mitochondria: Releasing Power for Life Review and Unleashing the Machineries of Death," Cell, 2003, pp. 481-490, vol. 112.
Olszewska et al., "Critical Review Mitochondria as a Pharmacological Target: Magnum Overview," IUBMB Life, 2013, pp. 273-281, vol. 65:3.
O'Connor et al., "Powders," Remington: The Science and Practice of Pharmacy, 2005. Lippincott, 21st Ed., pp. 702-928, Williams and Williams, Philadelphia.
Ott et al., "Mitochondria, oxidative stress and cell death," Apoptosis, 2007, pp. 913-922, vol. 12.
Park et al., "β-Lapachone—induced reactive oxygen species (ROS) generation mediates autophagic cell death in glioma U87 MG cells," Chemico-Biological Interactions, 2011, pp. 37-44, vol. 189.

A. MDA-MB-231 parental

B. MDA-MB-231 rho0

SUBSTITUTED β-LAPACHONES FOR TREATING CANCER

CROSS-REFERENCE TO RELATED APPLICATIONS

The present application is a Continuation of U.S. National Phase application Ser. No. 15/580,416, filed Jun. 8, 2016, now issued as U.S. Pat. No. 10,450,289 issued Oct. 22, 2019, which is a National Stage of International Patent Application No. PCT/US2016/036440, filed Jun. 8, 2016, which claims the benefit of U.S. Provisional Application No. 62/172,422, filed Jun. 8, 2015, each of which is incorporated herein by reference in its entirety.

STATEMENT REGARDING FEDERAL FUNDING

This invention was made with government support under Grant Nos. GM102989 and GM067082 awarded by the National Institute of Health. The government has certain rights in the invention.

BACKGROUND OF THE INVENTION

Mitochondria play important roles in tumor cell physiology and survival by providing energy and metabolites for growth and proliferation. As part of their oncogenic status, cancer cells frequently produce increased levels of mitochondrial-generated reactive oxygen species (ROS). However, extensive stimulation of ROS generation in mitochondria can induce cancer cell death, and is one of the major mechanisms of action of many anticancer agents.

Nitochondria control many growth and survival pathways in eukaryotic cells, not only as the major energy-producing organelle and a regulator of apoptosis and autophagy, but also as a source of steroids, hemes, amino acids, neurotransmitters, and organic acids. One side product of ATP production in the electron transfer chain (ETC) is the generation of up to 90% of total intracellular reactive oxygen species (ROS), including superoxide radical anion, hydroxyl radical, and reactive nitrogen species (RNS). ROS bursts can cause oxidative stress levels associated with acute and chronic damage to cellular components, including mitochondrial membrane lipids such as cardiolipin and mitochondrial DNA (mtDNA). Cumulative oxidative damage will result in functional aberrations of cellular metabolism and signaling pathways and various pathological disorders. However, rather than just representing a chemical nuisance and dangerous progenitor of lipid, protein, and DNA oxidation products, leading to apoptosis. ROS also mediate a diverse range of cellular processes such as signaling cascades, cell cycle control, and autophagy. In fact, controlled ROS release can serve as a modulator of redox-homeostasis and cell signaling pathways. Therefore, rather than complete abolition of ROS, controlled inflection of ROS levels may offer treatment options for a large number of diseases such as cancer, diabetes, cardiovascular and neurodegenerative disorders, where mitochondria have emerged as a key contributing factor.

Cancer cells apparently increase their ROS production relative to normal cells, which is believed to be essential for maintaining oncogenic signaling. Furthermore, disrupting redox homeostasis by either suppressing antioxidant enzymes or enhancing the ROS production in cancer cells has been shown to be able to induce cancer cell death and thus offers an effective strategy for cancer therapy. Directly or indirectly, ROS are also known to play important roles in the anticancer activities of many chemotherapeutic drugs. Unfortunately, these agents often fail to induce cell death in cancer cells due to alterations in their endogenous cell death signaling, such as the p53 pathway. Heat shock proteins compensating for oxidative stress are also frequently upregulated in cancer tissue. Therefore, agents that directly target mitochondria to induce mitochondria-initiated cell death are thought to have greater potential in circumventing tumor cell resistance compared to standard chemotherapeutic drugs. Furthermore, in addition to ROS production, other aspects of mitochondrial metabolism are also required for the function of many types of tumors, including melanoma. Induction of mitochondrial dysfunction is thus considered to be a promising strategy for cancer treatment.

BRIEF SUMMARY OF THE INVENTION

Provided herein are compounds and compositions comprising a mitochondria-targeting moiety and a β-lapachone or a derivative thereof. In one aspect, the mitochondria-targeting moiety is a membrane-active fragment of gramicidin S or an E-alkylene isostere thereof conjugated to a cargo, wherein the fragment of gramicidin S or E-alkylene isostere thereof has the sequence of one of: Leu-$^D$Phe-Pro-Val-Orn, Leu-(E)-$^D$Phe-Pro-Val-Orn, or acylated derivatives thereof, in which pendant amines are acylated or modified with an amine protecting group as indicated herein.

Provided herein is a compound including a mitochondria-targeting group covalently linked to β-lapachone or a β-lapachone derivative, and a salt or ester thereof, including pharmaceutically-acceptable salts or esters thereof. In some aspects, the compound includes a β-lapachone derivative. In further aspects, the β-lapachone derivative has the structure:

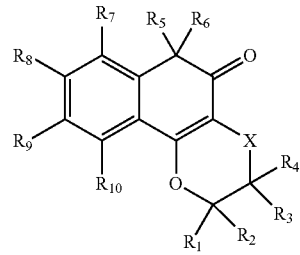

wherein X is —$(CH_2)_n$— where n=1-3, —S—, or —S—$CH_2$—; $R_1$, is H, OH, $C_1$-$C_6$ alkyl, $C_1$-$C_6$ alkenyl, $C_1$-$C_6$ alkoxy, $C_1$-$C_6$ alkoxycarbonyl, —$(CH_2)_n$-aryl, —$(CH_2)_n$-heteroaryl, —$(CH_2)_n$-phenyl, —ORa, unsubstituted or substituted alkylamino; unsubstituted or substituted dialkylamino, or substituted heterocycle, wherein Ra is H, unsubstituted or substituted amide, unsubstituted or substituted heterocycle, or substituted silyl; $R_2$ is H, OH, $C_1$-$C_6$ alkyl, $C_1$-$C_6$ alkenyl, $C_1$-$C_6$ alkoxy, $C_1$-$C_6$ alkoxycarbonyl, —$(CH_2)_n$-aryl, —$(CH_2)_n$-heteroaryl, —$(CH_2)_n$-phenyl, a carboxyacid, or a carboxy ester; $R_3$ and $R_4$ are, independently, H, OH, unsubstituted or substituted $C_1$-$C_6$ alkyl, unsubstituted or substituted $C_1$-$C_6$ alkenyl, unsubstituted and substituted $C_1$-$C_6$ alkoxy, unsubstituted or substituted $C_1$-$C_6$ acyl, $C_1$-$C_6$ alkoxycarbonyl, amino, alkylamino, dialkylamino, unsubstituted or substituted aryl, unsubstituted or substituted phenyl, unsubstituted or substituted benzyl, unsubstituted or substituted heteroaryl, or unsubstituted or substituted heterocycle, —$(CH_2)_n$-aryl, —$(CH_2)_n$-heteroaryl, or —$(CH_2)_n$-phenyl; $R_5$ is sulfonate and $R_6$ is hydroxyl, or $R_5$ and $R_6$, together, are carbonyl (=O); $R_7$, $R_8$, $R_9$, and $R_{10}$ are each, independently, H, halogen, hydroxyl, unsubstituted or substituted $C_1$-$C_6$ alkyl, unsubstituted or substituted $C_1$-$C_6$ alkoxy, $C_1$-$C_6$ alkoxycarbonyl, amino, alkylamino, dialkylamino, unsubstituted or substituted aryl, unsubstituted or substituted phenyl, unsubstituted or substituted benzyl, unsubstituted or substituted heteroaryl, or unsubstituted or substituted heterocycle, nitro, cyano, carboxyacid, or amide; wherein X is not C when $R_1$ and $R_2$ are methyl, $R_5$ and $R_6$, together are carbonyl, and $R_3$, $R_4$, $R_7$, $R_8$, $R_9$, and $R_{10}$ are H (that is, the β-lapachone derivative is not β-lapachone), or an isostere thereof, or a pharmaceutically acceptable salt or ester thereof.

In aspects, the β-lapachone or the β-lapachone derivative is linked to the mitochondria-targeting group at position $C_2$ or $C_3$. In some aspects, the β-lapachone or the β-lapachone derivative is linked to a mitochondria-targeting group at position $C_3$.

In aspects, the compound has a structure:

a.

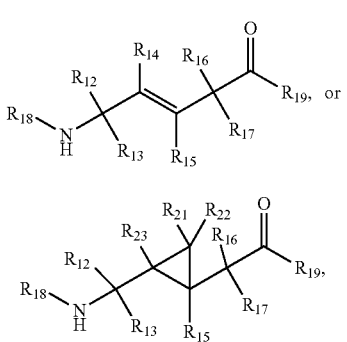

wherein $R_{12}$, $R_{13}$, $R_{16}$, and $R_{17}$ are independently hydrogen, hydroxyl, halo, a $C_1$-$C_6$ straight or branched-chain alkyl, or a $C_1$-$C_6$ straight or branched-chain alkyl further comprising a phenyl ($C_6H$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted, for example, and without limitation, $R_{12}$, $R_{13}$, $R_{16}$, and $R_{17}$ are independently methyl-, hydroxyl- or fluoro-substituted, including: methyl, ethyl, propyl, 2-propyl, butyl, t-butyl, pentyl, hexyl, benzyl, hydroxybenzyl (e.g., 4-hydroxybenzyl), phenyl, or hydroxyphenyl; $R_{15}$ is hydrogen, a halo, a $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted; $R_{18}$ is —C(O)—$R_{24}$, —C(O)O—$R_{24}$, or —P(O)—($R_{24}$)$_2$, wherein $R_{24}$ is $C_1$-$C_6$ straight or branched-chain alkyl or a $C_1$-$C_6$ straight or branched-chain alkyl optionally comprising one or more ($C_6H_5$) groups that are independently unsubstituted, or methyl-, ethyl-, hydroxyl-, halo-substituted or fluoro-substituted, for example and without limitation, $R_{18}$ is Ac (Acetyl, R=—C(O)—CH$_3$), Boc (R=—C(O)O-tert-butyl), Cbz (R=—C(O)O-benzyl (Bn)), or a diphenylphosphate group; $R_{19}$ is —NH—$R_{20}$, —O—$R_{20}$ or —CH$_2$—$R_{20}$, where $R_{20}$ is β-lapachone or a derivative thereof according to any aspect as described above; $R_{14}$ is a halo, a $C_1$-$C_6$ straight or branched-chain alkyl or a $C_1$-$C_6$ straight or branched-chain alkyl further comprising one or more ($C_6H_5$) groups that are independently unsubstituted, or methyl-, ethyl-, hydroxyl- or halo-substituted; and $R_{21}$, $R_{22}$, and $R_{23}$ are independently H or a halo;

b.

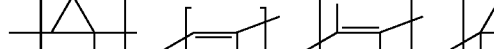

wherein X is $R_{12}$, $R_{13}$, $R_{16}$, $R_{17}$, and $R_{25}$ are each independently hydrogen, halo, a $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted; $R_{19}$ is —NH—$R_{20}$, —O—$R_{20}$ or —CH$_2$—$R_{20}$, where $R_{20}$ is β-lapachone or a derivative thereof according to any aspect as described above; and $R_{18}$ is —C(O)—$R_{24}$, —C(O)O—$R_{24}$, or —P(O)—($R_{24}$)$_2$, wherein $R_{24}$ is $C_1$-$C_6$ straight or branched-chain alkyl or a $C_1$-$C_6$ straight or branched-chain alkyl optionally comprising one or more ($C_6H_5$) groups that are independently unsubstituted, or methyl-, ethyl-, hydroxyl-, halo-substituted or fluoro-substituted, for example and without limitation, $R_{18}$ is Ac (Acetyl, R=—C(O)—CH$_3$), Boc (R—C(O)O-tert-butyl), Cbz (R=—C(O)O-benzyl (Bn)), or a diphenylphosphate group; or c.

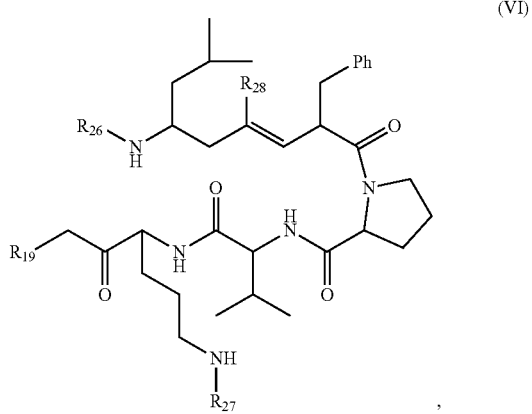

wherein $R_{19}$ is —NH—$R_{20}$, —O—$R_{20}$ or —CH$_2$—$R_{20}$, where $R_{20}$ is β-lapachone, or a β-lapachone derivative according to any aspect described above; $R_{26}$ and $R_{27}$, independently are an amine protecting group or acylated. In one aspect, $R_{26}$ and $R_{27}$ are protecting groups independently selected from the group consisting of: 9-fluorenylmethyloxy carbonyl (Fmoc), t-butyloxycarbonyl (Boc), benzhydryloxycarbonyl (Bhoc), benzyloxycarbonyl (Cbz), O-nitroveratryloxycarbonyl (Nvoc), benzyl (Bn), allyloxycarbonyl (alloc), trityl (Trt), 1-(4,4-dimethyl-2,6-dioxacyclohexylidene)ethyl (Dde), diathiasuccinoyl (Dts), benzothiazole-2-sulfonyl (Bts), dimethoxytrityl (DMT) and monomethoxytrityl (MMT), and $R_{28}$ is H or methyl. In one aspect, $R_{26}$ is Boc and $R_{27}$ is Cbz. Ph is phenyl.

In some aspects, the compound has the structure of (III) or (IV) above. In other aspects, the compound has the structure of (V) or (VI) above. In still further aspects, the compound has the structure of (VII) above.

In aspects, the compound has the structure:

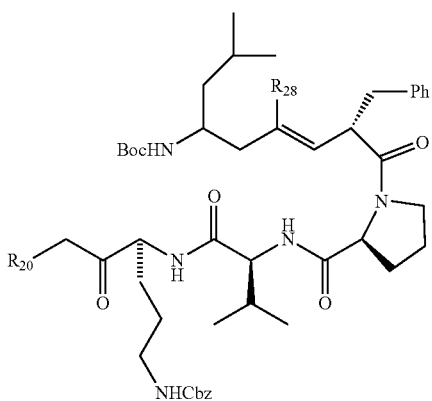

wherein $R_{19}$ is —NH—$R_{20}$, —O—$R_{20}$ or —CH$_2$—$R_{20}$, where $R_{20}$ is β-lapachone, or a β-lapachone derivative.

In aspects, the compound has the structure:

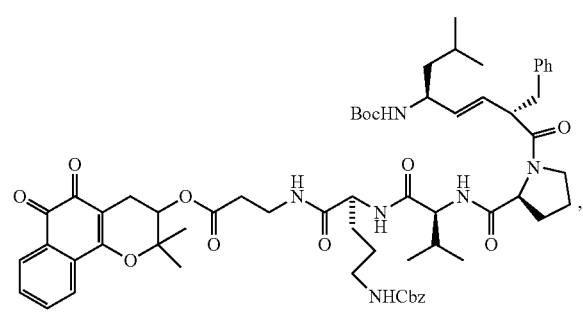

an isostere thereof, or a pharmaceutically acceptable salt or ester thereof.

Also provided herein is a composition including a first compound as described above and a pharmaceutically-acceptable excipient. In aspects the composition includes a second chemotherapeutic agent that is different from the first compound. In some aspects, the second chemotherapeutic agent is either β-lapachone, a β-lapachone derivative, abiraterone acetate, altretamine, amsacrine, anhydro vinblastine, auristatin, bafetinib, bexarotene, bicalutamide, BMS 184476, 2,3,4,5,6-pentafluoro-N-(3-fluoro-4-methoxyphenyl)benzene sulfonamide, bleomycin, bosutinib, busulfan, cachectin, cemadotin, chlorambucil, cyclophosphamide, 3',4'-didehydro-4'-deoxy-8'-norvin-caleukoblastine, docetaxol, doxetaxel, carboplatin, carmustine (BCNU), chlorambucil, cisplatin, cryptophycin, cyclophosphamide, cytarabine, dacarbazine (DTIC), dactinomycin, daunorubicin, decitabine dolastatin, doxorubicin (adriamycin), etoposide, etoposide phosphate, 5-fluorouracil, finasteride, flutamide, hydroxyurea, hydroxyureataxanes, ifosfamide, imatinib, irinotecan, liarozole, lonidamine, lomustine (CCNU), MDV3100, mechlorethamine (nitrogen mustard), melphalan, mitoxantrone, mivobulin isethionate, rhizoxin, sertenef, streptozocin, mitomycin, methotrexate, nilotinib, nilutamide, onapristone, oxaliplatin, paclitaxel, ponatinib, prednimustine, procarbazine, RPRI 09881, stramustine phosphate, tamoxifen, tasonermin, taxol, teniposide, topotecan, tretinoin, vinblastine, vincristine, vindesine sulfate, vinflunine, or pharmaceutically acceptable salts or esters thereof.

Also provided herein is a method of treating a cancer in a patient, including the step of administering to a patient an amount of a first compound according described above in an amount effective to increase reactive oxygen species (ROS) in mitochondria of cancer cells of a patient. In some aspects, the method further includes administering a radiation therapy to the patient while the first compound is present in the patient. In some aspects the method further includes administering a second chemotherapeutic agent that differs from the first compound. In further aspects, the second chemotherapeutic agent is either β-lapachone, a β-lapachone derivative, abiraterone acetate, altretamine, amsacrine, anhydro vinblastine, auristatin, bafetinib, bexarotene, bicalutamide, BMS 184476, 2,3,4,5,6-pentafluoro-N-(3-fluoro-4-methoxyphenyl)benzene sulfonamide, bleomycin, bosutinib, busulfan, cachectin, cemadotin, chlorambucil, cyclophosphamide, 3',4'-didehydro-4'-deoxy-8'-norvin-caleukoblastine, docetaxol, doxetaxel, carboplatin, carmustine (BCNU), chlorambucil, cisplatin, cryptophycin, cyclophosphamide, cytarabine, dacarbazine (DTIC), dactinomycin, daunorubicin, decitabine dolastatin, doxorubicin (adriamycin), etoposide, etoposide phosphate, 5-fluorouracil, finasteride, flutamide, hydroxyurea, hydroxyureataxanes, ifosfamide, imatinib, irinotecan, liarozole, lonidamine, lomustine (CCNU), MDV3100, mechlorethamine (nitrogen mustard), melphalan, mitoxantrone, mivobulin isethionate, rhizoxin, sertenef, streptozocin, mitomycin, methotrexate, nilotinib, nilutamide, onapristone, oxaliplatin, paclitaxel, ponatinib, prednimustine, procarbazine, RPRI 09881, stramustine phosphate, tasonermin, taxol, teniposide, topotecan, tretinoin, vinblastine, vincristine, vindesine sulfate, vinflunine, or pharmaceutically acceptable salts or esters thereof.

Also provided herein is a method of treating neurodegeneration, including the step of administering to a patient an amount of a compound as described above in an amount effective to decrease reactive oxygen species (ROS) production in mitochondria of a cell of a patient.

Also provided herein is a method of decreasing oxidative damage in a patient including the step of administering to a patient an amount of a compound as described above in an amount effective to decrease reactive oxygen species (ROS) production in mitochondria of a cell of a patient.

DETAILED DESCRIPTION OF THE INVENTION

Figure 1:
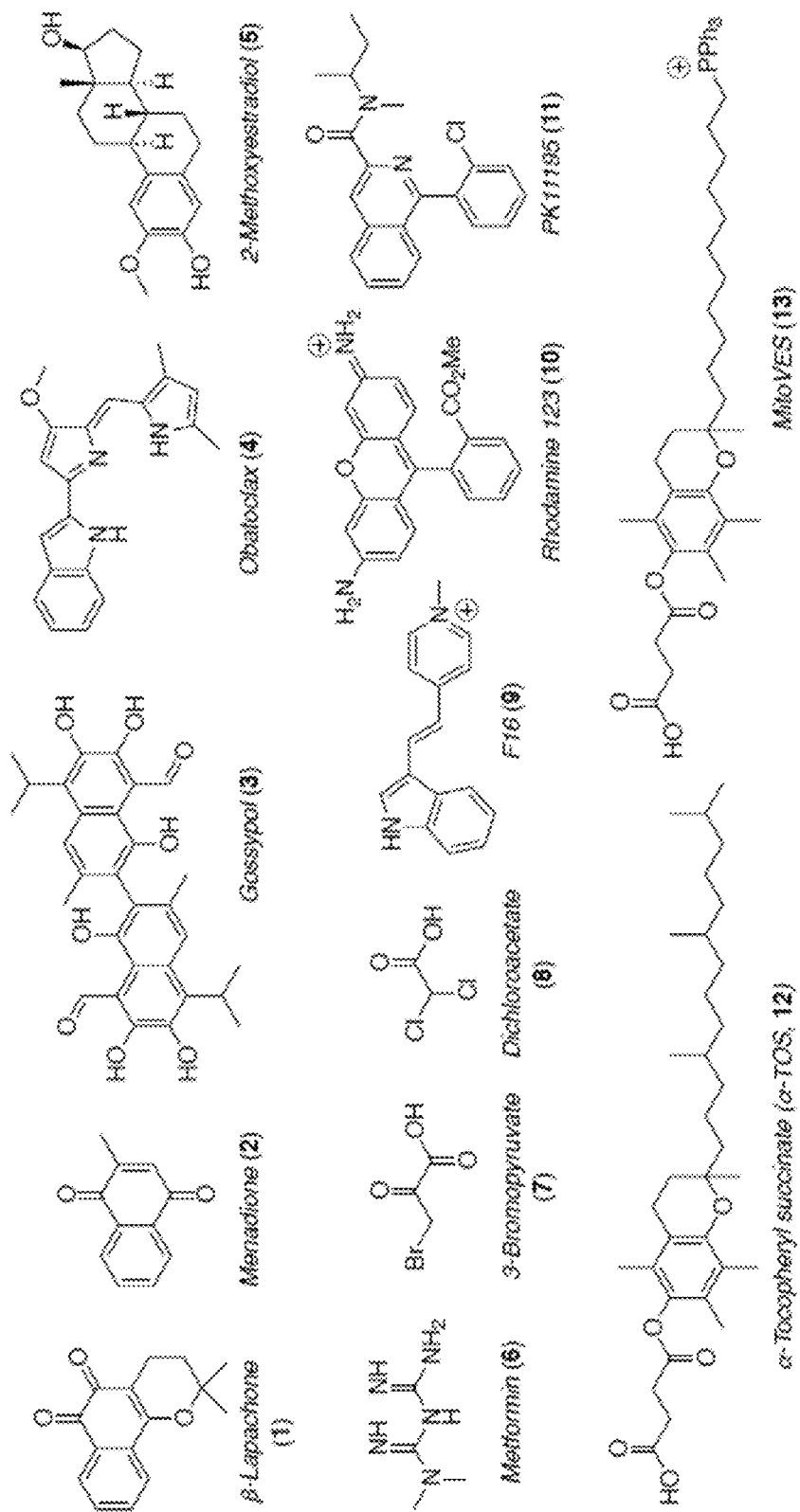
FIG. 1 shows a selection of mitocans-cytotoxic agents with mitochondrial targeted mechanisms of action.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions also refer to word forms, cognates and grammatical variants of those words or phrases.

As used herein, the terms "comprising," "comprise" or "comprised," and variations thereof, in reference to elements of an item, composition, apparatus, method, process, system, claim etc. are intended to be open-ended, meaning that the item, composition, apparatus, method, process, system, claim etc. includes those elements and other elements can be included and still fall within the scope/definition of the described item, composition, apparatus, method, process, system, claim etc. As used herein, "a" or "an" means one or more. As used herein "another" may mean at least a second or more.

As used herein, the terms "patient" or "subject" refer to members of the animal kingdom including but not limited to human beings.

A "mitochondrial targeting group" is a moiety (that is, a part of a molecule) that partitions specifically to mitochondria. In one aspect, a mitochondria targeting group is a membrane active peptide fragment derived from an antibiotic molecule that acts by targeting a bacterial cell wall.

Examples of such antibiotics include: bacitracins, gramicidins, valinomycins, enniatins, alamethicins, beauvericin, serratomolide, spodriesmolide, tyrocidins, polymyxins, monamycins, and lissoclinum peptides. The membrane-active peptide fragment derived from an antibiotic may comprise a complete antibiotic polypeptide, or a portion thereof having itochondria-targeting abilities, which is readily determined, for example, by cellular partitioning experiments using radiolabeled peptides. Examples of useful gramicidin-derived membrane active peptide fragments are the Leu-$^D$Phe-Pro-Val-Orn and $^D$Phe-Pro-Val-Orn-Leu bemigramicidin fragments. As gramicidin is cyclic, any hemigrarnicidin 5-mer is expected to be useful as a membrane active peptide fragment, including Leu-$^D$Phe-Pro-Val-Orn, $^D$Phe-Pro-Val-Orn-Leu, Pro-Val-Orn-Leu-$^D$phe, Val-Orn-Leu-$^D$Phe-Pro and Orn-Leu-$^D$Phe-Pro-Val (from gramicidin S). Any larger or smaller fragment of gramicidin, or even larger fragments containing repeated granicidin sequences (e.g. Leu-$^D$Phe-Pro-Val-Orn-Leu-$^D$Phe-Pro-Val-Orn-Leu-$^D$Phe-Pro) are expected to be useful for membrane targeting, and can readily tested for such activity. In one aspect, the gramicidin S-derived peptide comprises a β-turn, which appears to confer to the peptide a high affinity for mitochondria. Derivatives of granicidin, or other antibiotic fragments, include isosteres (molecules or ions with the same number of atoms and the same number of valence electrons—as a result, they can exhibit similar pharmacokinetic and pharmacodynamic properties), such as (E)-alkene isosteres (see, United States Patent Publication Nos. 2007/0161573 and 2007/0161544 incorporated herein by reference in their entirety, for exemplary synthesis methods). As with Gramicidin, the structure (amino acid sequence) of bacitracins, other gramicidins, valinomycins, enniatins, alanethicins, beauvericin, serratomolide, sporidesmolide, tyrocidins, polyrnyxins, monamycins, and lissoclinurn peptides are all broadly-known, and fragments of these can be readily prepared and their membrane-targeting abilities can easily be confirmed by a person of ordinary skill in the art.

In another aspect, peptide isosteres, e.g., of a portion of gramicidin S are employed as mitochondria-targeting groups. Among the suitable peptide isosteres are trisubstituted (E)-alkene peptide isosteres and cyclopropane peptide isosteres, as well as all imine addition products of hydro- or carbometalated internal and terminal alkynes for the synthesis of d-i and trisubstituted (E)-alkene and cyclopropane peptide isosteres (See Wipf et al. Imine additions of internal alkynes for the synthesis of trisubstituted (E)-alkene and cyclopropane isosteres, Adv Synth Catal. 2005, 347:1605-1613). These peptide mimetics have been found to act as β-turn promoters (See Wipf et al. Convergent Approach to (E)-Alkene and Cyclopropane Peptide Isosteres, Org Lett. 2005, 7(1):103-106).

The marked differences between normal and cancer cells in mitochondrial metabolism and function provide support for the hypothesis that selectivity, as well as high therapeutic efficacy can be accomplished by direct targeting of mitochondria. In fact, targeting the electron transfer chain (ETC) in mitochondria with synthetic and natural toxins has attracted significant recent interest. Several classes of mitochondrial targeted anticancer agents, known as 'mitocans', have been reported and categorized into eight classes depending on their sites of action, i.e. 1) hexokinase inhibitors; 2) Bcl-2 family protein ligands; 3) thiol redox system disruptors; 4) mitochondrial membrane transporter/channel inhibitors; 5) electron transfer chain deregulators; 6) inner mitochondrial membrane disruptors; 7) TCA cycle inhibitors; and 8) mtDNA damaging agents (FIG. 1). Most of these targets are closely correlated to cancer specific alterations of mitochondial functions and bioenergetics.

In one aspect, an alkene peptide isostere segment of the antibiotic gramicidin S (GS), i.e. the XJB-peptide, acts as an effective mitochondrial targeting vector. The presence of a type II' β-turn in this pentapeptide sequence facilitates membrane permeability since the polar functionality of the backbone is less solvent exposed. After several structural modifications, the mitochondrial targeting antioxidant nitroxide, XJB-5-131, was developed as a first generation lead compound and a promising therapeutic agent. In parallel to these efforts to generate mitochondrial targeted anti-neurodegenerative compounds, development of a mitochondrial targeted ROS inducer for anticancer therapy has begun. A principal concern with ROS inducers in cancer therapy is whether these compounds have preferential affinities to localize and achieve sufficient concentrations for efficacy within the mitochondrial targets of malignant cells. Due to the distinct features of mitochondrial membranes, major challenges and strategies for a successful treatment rely on the design of effective delivery systems that can penetrate mitochondrial membrane barriers. Toward this goal, various chemistry-based approaches to targeting mitochondria have been reported. The most widely used strategy for the delivery of organic molecules targeting mitochondria is the use of lipophilic cationic phosphonium ions, which are attracted by the large inner mitochondrial membrane potential and accumulate within the negatively charged mitochondrial matrix. Conjugation of bioactive molecules to peptide-based MT (mitochondria) targeting sequence, such as SS-peptides, mitochondria-penetrating peptides (MPPs), synthetic peptides and amino acid-based transporters are also major strategies for MT delivery. Additionally, the use of targeting systems with nanoparticles and liposomes is expanding. While therapeutic success has been limited, these early results provide support for additional investigations for the design of mitochondrial targeted anticancer drugs. For example, a TPP-tagged dichloroacetate showed three orders of magnitude enhanced potency and cancer cell specificity.

In order to generate a highly effective redox cycling system through direct targeting of mitochondria, an electron-rich ortho-quinone, β-lapachone (I, also 1 in FIG. 1), was selected for the payload portion of the mitochondrial targeting platform. Numbering of β-lapachone derivatives correspond to the numbering of Formula I. Quinones are frequently involved in redox cycling and glutathione depletion after reductive activation by enzymes, generating bursts of ROS in addition to serving as electrophilic alkylators. β-lapachone (also, 2,2-dimethyl-3,4-dihydro-2H-benzo[h]chromene-5,6-dione, CAS 4707-32-8) is a tricyclic ortho-naphthoquinone compound having the structure depicted in Formula I.

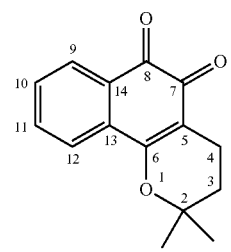

Formula I

β-lapachone is a naturally occurring ortho-naphthoquinone isolated from the lapacho tree (*Tabebuia avellanedae*) that has shown a range of potent biological activities relevant to antibacterial, antifungal, anti-inflammatory, and antitumor pathways. ARQ761, a β-lapachone analog, has entered Phase I/II clinical trials for several types of cancer either as a single agent or in combination with other chemotherapeutics. The cytotoxic effects of β-lapachone are derived from ROS generation dependent on the action of cytosolic NAD(P)H:quinone oxireductase 1 (NQO1) which reduces β-lapachone to a reactive hydroquinone and semiquinone redox-cycler. Since cellular levels of NQO1 vary between cell types, especially between normal and cancer cells, β-lapachone can selectively kill NQO1 over-expressing cancer cells.

Hence, it is hypothesized that a targeted delivery of β-lapachone to mitochondria would 1) provide further insight into the mechanism of action of the active species; 2) trigger a specific activation of a more defined molecular cell death mechanism; 3) provide a novel mitocan causing mitochondrial dysfunction and therefore potentially broadening its therapeutic profile in cancer treatment; and, 4) shed light on the hypothesis that small quantities of ROS generated in mitochondrial might active protective cellular signaling pathways.

A very large number of β-lapachone derivatives exhibiting anti-neoplastic, antifungal, and/or antiviral activity, and/or other pharmacologically-relevant activities, have been described, including methods of synthesis of those derivatives. Those β-lapachone derivatives are all expected to be pharmacologically-active (e.g., as an antineoplastic, antifungal, antiviral, etc. therapeutic composition and as a drug product) when incorporated into the compositions, described herein. Relative to the β-lapachone structure of Formula I, above, those derivatives include: modification of one or both of the methyl groups at $C_2$ and/or addition of one or more groups at C3 (See, e.g., U.S. Pat. Nos. 5,763,625; 5,824,700; and 5,969,163 incorporated herein by reference for their disclosure of β-lapachone derivatives); modification of the size of the hetero ring to have from five to seven members, and/or modification of the composition of the hetero-ring by substituting a carbon for an additional hetero-atom, or adding a hetero-atom, e.g., with S inserted between $C_4$ and $C_5$, or with S replacing $C_4$ (See, e.g., U.S. Pat. Nos. 8,068, 459 and 5,969,163 incorporated herein by reference for their disclosure of 3-lapachone derivatives); Addition of a double bond to the hetero-ring having five members (See, e.g., U.S. Pat. No. 5,969,163 incorporated herein by reference for its disclosure of β-lapachone derivatives); and/or replacement of the carbonyl group at C8 with a sulfonate and a hydroxyl group (8-hydroxyl, 8-sulfonate (See, e.g., U.S. Pat. No. 7,790,765 incorporated herein by reference for its disclosure of β-lapachone derivatives). β-lapachone and its derivatives also include salts thereof, including pharmaceutically- or verterinarily-acceptable salts thereof.

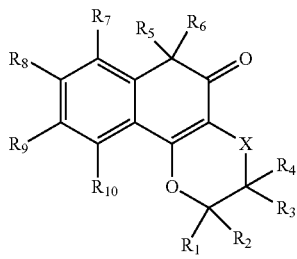

(II)

wherein

X is $—(CH_2)_n—$ where n=0-3, —S—, or —S—$CH_2$—;

$R_1$, $R_2$, $R_3$ and $R_4$ are, independently, H, $C_1$-$C_6$ alkyl, $C_1$-$C_6$ alkenyl, $C_1$-$C_6$ alkoxy, $C_1$-$C_6$ alkoxycarbonyl, $—(CH_2)_n$-aryl, $—(CH_2)_n$-heteroaryl, $—(CH_2)_n$-phenyl, and in one aspect, $R_3$ is H and $R_4$ is OH, and in one aspect, $R_1$ is $—C—R_{11}$, where $R_{11}$ is H, 0; and $R_5$ is sulfonate and $R_6$ is hydroxyl, or $R_5$ and $R_6$, together, are carbonyl (=O), and wherein, in one aspect, the β-lapachone derivatives are linked to a mitochondria-targeting group at positions $C_2$ or $C_3$, e.g., via $R_1$, $R_2$, $R_3$, or $R_4$, and in one aspect, at position $C_3$, that is via $R_3$ or $R_4$.

$R_7$, $R_8$, $R_9$ and $R_{10}$ are, independently, H, halogens, hydroxy, $C_1$-$C_6$ alkyl, $C_1$-$C_6$ alkenyl, $C_1$-$C_6$ alkoxy, $C_1$-$C_6$ alkoxycarbonyl, $—(CH_2)_n$-aryl, $—(CH_2)_n$-heteroaryl, and $—(CH_2)_n$-phenyl.

In one aspect, the mitochondria-targeting moiety is a membrane-active fragment of gramicidin S or an E-alkylene isostere thereof conjugated to a cargo, wherein the fragment of gramicidin S or E-alkylene isostere thereof has the sequence of one of: Leu-$^D$Phe-Pro-Val-Orn, Leu-(E)-$^D$Phe-Pro-Val-Orn, or acylated derivatives thereof, in which pendant amines are acylated or modified with an amine protecting group as indicated herein.

In another aspect, the compound has the structure:

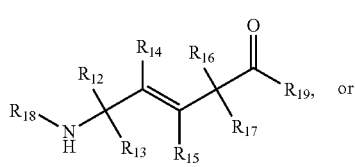

(III)

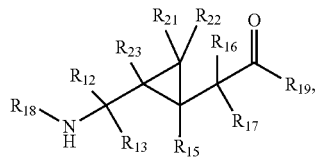

(IV)

wherein $R_{12}$, $R_{13}$, $R_{16}$, and $R_{17}$ are independently hydrogen, hydroxyl, halo, a $C_1$-$C_6$ straight or branched-chain alkyl, or a $C_1$-$C_6$ straight or branched-chain alkyl further comprising a phenyl ($C_6H$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted, for example, and without limitation, $R_{12}$, $R_{13}$, $R_{16}$, and $R_{17}$ are independently methyl-, hydroxyl- or fluoro-substituted, including: methyl, ethyl, propyl, 2-propyl, butyl, t-butyl, pentyl, hexyl, benzyl, hydroxybenzyl (e.g., 4-hydroxybenzyl), phenyl, or hydroxyphenyl; $R_{15}$ is hydrogen, a halo, a $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted;

$R_{18}$ is —C(O)—$R_{24}$, —C(O)O—$R_{24}$, or —P(O)—$(R_{24})_2$, wherein $R_{24}$ is $C_1$-$C_6$ straight or branched-chain alkyl or a $C_1$-$C_6$ straight or branched-chain alkyl optionally comprising one or more ($C_6H_5$) groups that are independently unsubstituted, or methyl-, ethyl-, hydroxyl-, halo-substituted or fluoro-substituted, for example and without limitation, $R_{18}$ is Ac (Acetyl, R=—C(O)—$CH_3$), Boc (R—C(O)O-tert-butyl), Cbz (R=—C(O)O-benzyl (Bn)), or a diphenylphosphate group;

$R_{19}$ is —NH—$R_{20}$, —O—$R_{20}$ or —$CH_2$—$R_{20}$, where $R_{20}$ is β-lapachone or a derivative thereof according to any aspect as described above;

$R_{14}$ is a halo, a $C_1$-$C_6$ straight or branched-chain alkyl or a $C_1$-$C_6$ straight or branched-chain alkyl further comprising one or more ($C_6H_5$) groups that are independently unsubstituted, or methyl-, ethyl-, hydroxyl- or halo-substituted; and $R_{21}$, $R_{22}$, and $R_{23}$ are independently H or halogens (See, e.g., International Patent Publication Nos. WO 2010/009405 and WO 2012/112851, incorporated herein by reference in their entirety).

In another aspect, the compound has the structure:

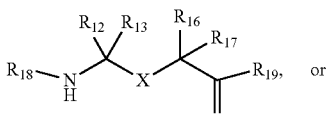

(V)

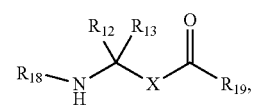

(VI)

wherein X is

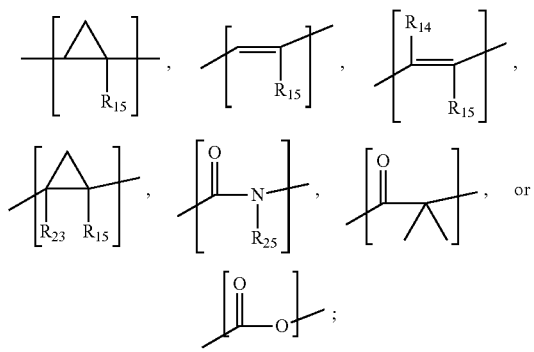

$R_{12}$, $R_{13}$, $R_{16}$, $R_{17}$, and $R_{25}$ are each independently hydrogen, halo, a $C_1$-$C_6$ straight or branched-chain alkyl, or a $C_1$-$C_6$ straight or branched-chain alkyl further comprising a phenyl ($C_6H_5$) group, wherein the $C_1$-$C_6$ straight or branched-chain alkyl group or the $C_1$-$C_6$ straight or branched-chain alkyl group comprising a phenyl group is unsubstituted or is methyl-, hydroxyl- or halo-substituted;

$R_{19}$ is —NH—$R_{20}$, —O—$R_{20}$ or —$CH_2$—$R_{20}$, where $R_{20}$ is β-lapachone or a derivative thereof according to any aspect as described above; and $R_{18}$ is —C(O)—$R_{24}$, —C(O)O—$R_{24}$, or —P(O)—$(R_{24})_2$, wherein $R_{24}$ is $C_1$-$C_6$ straight or branched-chain alkyl or a $C_1$-$C_6$ straight or branched-chain alkyl optionally comprising one or more ($C_6H_5$) groups that are independently unsubstituted, or methyl-, ethyl-, hydroxyl-, halo-substituted or fluoro-substituted, for example and without limitation, $R_{18}$ is Ac (Acetyl, R=—C(O)—$CH_3$), Boc (R—C(O)O-tert-butyl), Cbz (R=—C(O)O-benzyl (Bn)), or a diphenylphosphate group.

Non-limiting examples of compounds according to (V) include:

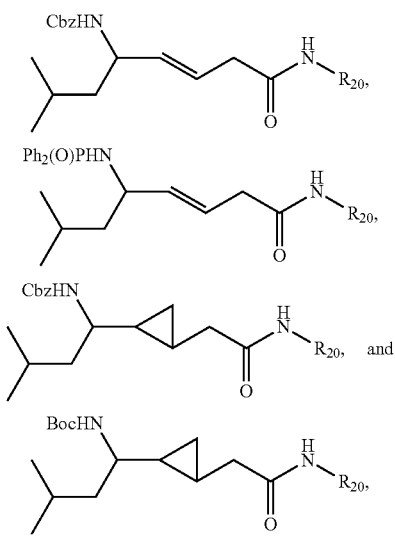

wherein $R_{20}$ is β-lapachone, or a β-lapachone derivative according to any aspect described above.

In one aspect, the compound has the structure:

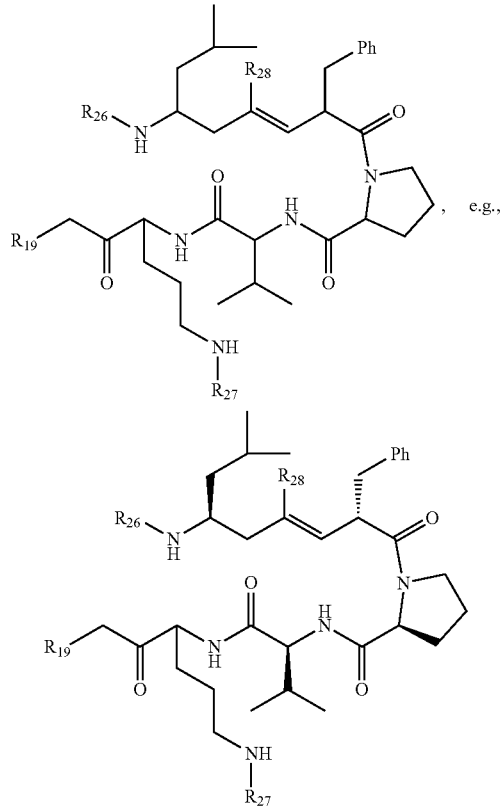

wherein $R_{19}$ is —NH—$R_{20}$, —O—$R_{20}$ or —$CH_2$—$R_{20}$, where $R_{20}$ is β-lapachone or a derivative thereof according to any aspect as described above; $R_{26}$ and $R_{27}$, independently are an amine protecting group or acylated. In one aspect, $R_{26}$ and $R_{27}$ are protecting groups independently selected from the group consisting of: 9-fluorenylmethyloxy carbonyl (Fmoc), t-butyloxycarbonyl (Boc), benzhydryloxycarbonyl (Bhoc), benzyloxycarbonyl (Cbz), O-nitroveratryloxycarbonyl (Nvoc), benzyl (Bn), allyloxycarbonyl (alloc), trityl (Trt), 1-(4,4-dimethyl-2,6-dioxacyclohexylidene)ethyl (Dde), diathiasuccinoyl (Dts), benzothiazole-2-sulfonyl (Bts), dimethoxytrityl (DMT) and monomethoxytrityl (MMT), and $R_{28}$ is H or methyl. In one aspect, $R_{26}$ is Boc and $R_{27}$ is Cbz. Ph is phenyl.

In another aspect, the compound has the structure:

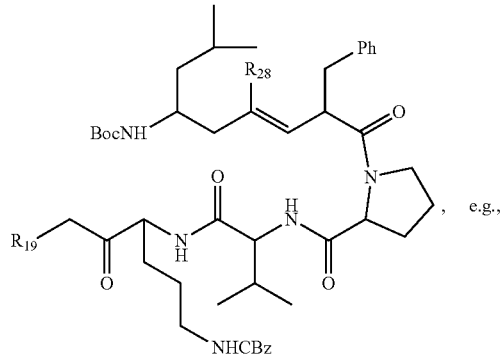

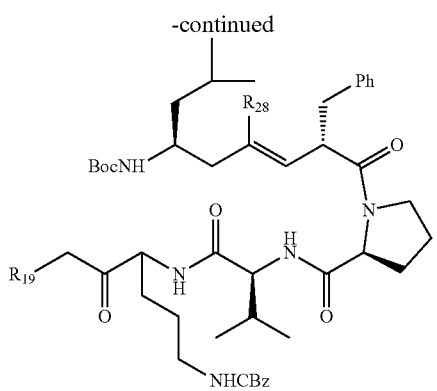

wherein $R_{19}$ is —NH—$R_{20}$, —O—$R_{20}$ or —CH$_2$—$R_{20}$, where $R_{20}$ is β-lapachone, or a β-lapachone derivative according to any aspect described above.

In another aspect, the mitochondria-targeting group has the structure:

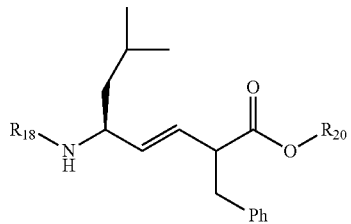

wherein $R_{17}$ is β-lapachone or a β-lapachone derivative, as described herein, and $R_{21}$ is an amine protecting group or acylated as described above for $R_{18}$ and $R_{19}$. In one aspect, $R_{21}$ is Boc or Cbz and $R_{20}$ is β-lapachone, and in another $R_{21}$ is Boc and $R_{20}$ is β-lapachone.

As used herein, unless indicated otherwise, for instance in a structure, all compounds and/or structures described herein comprise all possible stereoisomers, individually or mixtures thereof.

The following are exemplary definitions of various structural elements described herein.

As used herein, "alkyl" refers to straight, branched chain, or cyclic hydrocarbon groups including from 1 to about 20 carbon atoms, for example and without limitation $C_{1-3}$, $C_{1-6}$, $C_{1-10}$ groups, for example and without limitation, straight, branched chain alkyl groups such as methyl, ethyl, propyl, butyl, pentyl, hexyl, heptyl, octyl, nonyl, decyl, undecyl, dodecyl, and the like. "Substituted alkyl" refers to alkyl substituted at 1 or more, e.g., 1, 2, 3, 4, 5, or even 6 positions, which substituents are attached at any available atom to produce a stable compound, with substitution as described herein. "Optionally substituted alkyl" refers to alkyl or substituted alkyl. "Halogen," "halide," and "halo" refers to —F, —Cl, —Br, and/or —I. "Alkylene" and "substituted alkylene" refer to divalent alkyl and divalent substituted alkyl, respectively, including, without limitation, ethylene (—CH$_2$—CH$_2$—). "Optionally substituted alkylene" refers to alkylene or substituted alkylene.

"Alkene or alkenyl" refers to straight, branched chain, or cyclic hydrocarbyl groups including from 2 to about 20 carbon atoms, such as, without limitation $C_{1-3}$, $C_{1-6}$, $C_{1-10}$ groups having one or more, e.g., 1, 2, 3, 4, or 5, carbon-to-carbon double bonds. "Substituted alkene" refers to alkene substituted at 1 or more, e.g., 1, 2, 3, 4, or 5 positions, which substituents are attached at any available atom to produce a stable compound, with substitution as described herein. "Optionally substituted alkene" refers to alkene or substituted alkene. Likewise, "alkenylene" refers to divalent alkene. Examples of alkenylene include without limitation, ethenylene (—CH=CH—) and all stereoisomeric and conformational isomeric forms thereof. "Substituted alkenylene" refers to divalent substituted alkene. "Optionally substituted alkenylene" refers to alkenylene or substituted alkenylene.

"Alkyne or "alkynyl" refers to a straight or branched chain unsaturated hydrocarbon having the indicated number of carbon atoms and at least one triple bond. Examples of a ($C_2$-$C_8$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below. The term "alkynylene" refers to divalent alkyne. Examples of alkynylene include without limitation, ethynylene, propynylene. "Substituted alkynylene" refers to divalent substituted alkyne.

The term "alkoxy" refers to an —O-alkyl group having the indicated number of carbon atoms. For example, a ($C_1$-$C_6$)alkoxy group includes —O-methyl (methoxy), —O-ethyl (ethoxy), —O— propyl (propoxy), —O-isopropyl (isopropoxy), —O-butyl (butoxy), —O-sec-butyl (sec-butoxy), —O-tert-butyl (tert-butoxy), —O-pentyl (pentoxy), —O-isopentyl (isopentoxy), —O-neopentyl (neopentoxy), —O-hexyl (hexyloxy), —O-isohexyl (isohexyloxy), and —O-neohexyl (neohexyloxy). "Hydroxyalkyl" refers to a ($C_1$-$C_{10}$)alkyl group wherein one or more of the alkyl group's hydrogen atoms is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH, and branched versions thereof. The term "ether" or "oxygen ether" refers to ($C_1$-$C_{10}$)alkyl group wherein one or more of the alkyl group's carbon atoms is replaced with an —O— group. The term ether includes —CH$_2$—(OCH$_2$—CH$_2$)$_q$OP$_1$ compounds where P$_1$ is a protecting group, —H, or a ($C_1$-$C_{10}$)alkyl. Exemplary ethers include polyethylene glycol, diethylether, methylhexyl ether and the like.

"Aryl," alone or in combination refers to an aromatic monocyclic or bicyclic ring system such as phenyl or naphthyl. "Aryl" also includes aromatic ring systems that are optionally fused with a cycloalkyl ring. A "substituted aryl" is an aryl that is independently substituted with one or more substituents attached at any available atom to produce a stable compound, wherein the substituents are as described herein. "Optionally substituted aryl" refers to aryl or substituted aryl. "Arylene" denotes divalent aryl, and "substituted arylene" refers to divalent substituted aryl. "Optionally substituted arylene" refers to arylene or substituted arylene.

"Heteroatom" refers to N, O, P and S. Compounds that contain N or S atoms can be optionally oxidized to the corresponding N-oxide, sulfoxide or sulfone compounds. "Hetero-substituted" refers to an organic compound in any embodiment described herein in which one or more carbon atoms are substituted with N, O, P or S.

"Substituted" or "substitution" refer to replacement of a hydrogen atom of a molecule or an R-group with one or more additional R-groups such as halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, nitro, sulfato or other R-groups.

"Cycloalkyl" refer to monocyclic, bicyclic, tricyclic, or polycyclic, 3- to 14-membered ring systems, which are either saturated, unsaturated or aromatic. The cycloalkyl group may be attached via any atom. Cycloalkyl also contemplates fused rings wherein the cycloalkyl is fused to an aryl or hetroaryl ring. Representative examples of cycloalkyl include, but are not limited to cyclopropyl, cyclobutyl, cyclopentyl, and cyclohexyl. A cycloalkyl group can be unsubstituted or optionally substituted with one or more substituents as described herein below. "Cycloalkylene" refers to divalent cycloalkyl. The term "optionally substituted cycloalkylene" refers to cycloalkylene that is substituted with 1, 2 or 3 substituents, attached at any available atom to produce a stable compound, wherein the substituents are as described herein.

"Carboxyl" or "carboxylic" refers to group having the indicated number of carbon atoms and terminating in a —C(O)OH group, thus having the structure —R—C(O)OH, where R is a divalent organic group that includes linear, branched, or cyclic hydrocarbons. Non-limiting examples of these include: $C_{1-8}$ carboxylic groups, such as ethanoic, propanoic, 2-methylpropanoic, butanoic, 2,2-dimethylpropanoic, pentanoic, etc.

"$(C_3-C_8)$aryl-$(C_1-C_6)$alkylene" refers to a divalent alkylene wherein one or more hydrogen atoms in the $C_1-C_6$ alkylene group is replaced by a $(C_3-C_8)$aryl group. Examples of $(C_3-C_8)$aryl-$(C_1-C_6)$alkylene groups include without limitation 1-phenylbutylene, phenyl-2-butylene, 1-phenyl-2-methylpropylene, phenylmethylene, phenylpropylene, and naphthylethylene. The term "$(C_3-C_8)$cycloalkyl-$(C_1-C_6)$alkylene" refers to a divalent alkylene wherein one or more hydrogen atoms in the $C_1-C_6$ alkylene group is replaced by a $(C_3-C_8)$cycloalkyl group. Examples of $(C_3-C_8)$cycloalkyl-$(C_1-C_6)$alkylene groups include without limitation 1-cyclproylbutylene, cycloproyl-2-butylene, cyclopentyl-1-phenyl-2-methylpropylene, cyclobutylmethylene and cyclohexylpropylene.

"Halo" refers to halogens, including F, Cl, Br, and I.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned herein are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely the salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like. The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen.

Pharmaceutically acceptable counterions include chloro, bromo, iodo, trifluoroacetate and acetate. The counterion of choice can be introduced using ion exchange resins.

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_1-C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and valyl.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art.

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

As used herein, unless indicated otherwise, for instance in a structure, all compounds and/or structures described herein comprise all possible stereoisomers, individually or mixtures thereof. The compound and/or structure may be an enantiopure preparation consisting essentially of an (−) or (+) enantiomer of the compound, or may be a mixture of enantiomers in either equal (racemic) or unequal proportions.

As used herein, a ring structure showing a bond/group that is not attached to any single carbon atom, for example and without limitation, depicted as

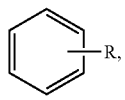

can be substituted at any position with one or more groups designated "R", and, unless indicated otherwise, each instance of R on the ring can be (independently) the same or different from other R moieties on the ring. Thus, if R is H, the group contains nothing but H groups. If R is "halo", it is a single halo (e.g., F, Cl, Br and I) group. If R is one or more independently of halo and CN, the ring may comprise one, two, three, four, halo or CN groups, such as, for example and without limitation: 2, 3, 4, or 5 chloro; 2, 3, 4, or 5 bromo; 2, 3- or 3,4- or 4,5- or 2,4-dichloro; 3-bromo-4-chloro; 3-bromo-4-cyano, and any other possible permutation of the listed groups.

Protected derivatives of the disclosed compounds also are contemplated. Many suitable protecting groups for use with the disclosed compounds are broadly-known in the art. In general, protecting groups are removed under conditions which will not affect the remaining portion of the molecule. These methods are well known in the art and include acid hydrolysis, hydrogenolysis and the like. One method involves the removal of an ester, such as cleavage of a phosphonate ester using Lewis acidic conditions, such as in TMS-Br mediated ester cleavage to yield the free phosphonate. A second method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with any of the large number of broadly-available publications. When an amine is deprotected, the resulting salt can readily be neutralized to yield the free amine. Similarly, when an acid moiety, such as a phosphonic acid moiety is unveiled, the compound may be isolated as the acid compound or as a salt thereof.

According to one aspect, amine side chains are protected using protective groups, for example and without limitation by acylation (See, e.g., U.S. Pat. Nos. 7,528,174; 7,718,603; and 9,006,186, and International Patent Publication Nos. WO 2010/009405 and WO 2012/112851, incorporated herein by reference in their entirety). Protecting groups are known in the art and include, without limitation: 9-fluorenylmethyloxy carbonyl (Fmoc), t-butyloxycarbonyl (Boc), benzhydryloxycarbonyl (Bhoc), benzyloxycarbonyl (Cbz), O-nitroveratryloxycarbonyl (Nvoc), benzyl (Bn), allyloxycarbonyl (alloc), trityl (Trt), 1-(4,4-dimethyl-2,6-dioxacyclohexylidene)ethyl (Dde), diathiasuccinoyl (Dts), benzothiazole-2-sulfonyl (Bts), dimethoxytrityl (DMT) and monomethoxytrityl (MMT) groups. A protecting group also includes acyl groups, such as acetyl groups, for example, as described.

The compounds typically are administered in an amount and dosage regimen to treat (a) a cancer (e.g., a malignancy), which includes, without limitation, any abnormal cells that divide without control and can invade nearby tissues, or (b) a hyperplasia, which is an increase in the number of cells in an organ or tissue, where the cells appear normal, and are not a cancer, but may become cancer. The compounds also are useful in reducing ROS production and/or the impact of ROS production, e.g., for treating neurodegeneration by virtue of their ability to reduce ROS damage at lower concentrations. For example, at concentrations of 1 μM or less XJB-lapachone decreased ROS as described in the examples below. Treatment of neurodegeneration includes treatment of neurodegenerative diseases, such as Parkinson's disease (PD), Alzheimer's disease (AD), Multiple Sclerosis (MS) and amyotrophic lateral sclerosis (ALS). The compounds may be administered in any manner that is effective to treat, mitigate or prevent any of the above conditions, including cancer, hyperplasia, neurodegeneration, PD, AD, MS, and ALS. Examples of delivery routes include, without limitation: topical, for example, epicutaneous, inhalational, enema, ocular, otic and intranasal delivery; enteral, for example, orally, by gastric feeding tube and rectally; and parenteral, such as, intravenous, intraarterial, intramuscular, intracardiac, subcutaneous, intraosseous, intradermal, intrathecal, intraperitoneal, transdermal, iontophoretic, transmucosal, epidural and intravitreal, with oral, intravenous, intramuscular and transdermal approaches being preferred in many instances.

As indicated above, and in the examples, depending upon the dosage of the compounds, the compounds can exhibit ROS-inhibiting activities, e.g., at low doses equivalent to 1 µM or less in a patient (that is, ranging from >0 µM up to, and including 1 µM) of the XJB-lapachone compound described in the examples below. At higher concentrations, e.g., the equivalent to >1.0 µM for XJB-lapachone described in the examples below, the compounds described herein increase ROS production in the mitochondria and due to the altered mitochondrial function and ROS metabolism in cancer cells compared to normal cells, will preferentially attack and kill the cancer cells. In one aspect the concentration of XJB-lapachone effective to increase ROS production in the mitochondria is, >2.0 µM, for example 2.5 µM and greater Therefore, an "effective amount" of the compound or composition described herein is an amount effective in a dosage regimen (amount of the compound and timing of delivery), to achieve a desired end-point, such as maintaining concentrations at a site of treatment within a range effective to achieve an outcome. Suitable outcomes include killing of cancer cells, improvement or maintenance of neurological function, neuroprotection, shrinking a tumor, or reducing ROS levels.

The compounds may be compounded or otherwise manufactured into a suitable composition for use, such as a pharmaceutical dosage form or drug product in which the compound is an active ingredient. Compositions may comprise a pharmaceutically acceptable carrier, or excipient. An excipient is an inactive substance used as a carrier for the active ingredients of a medication. Although "inactive," excipients may facilitate and aid in increasing the delivery or bioavailability of an active ingredient in a drug product. Non-limiting examples of useful excipients include: antiadherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts.

Useful dosage forms include: intravenous, intramuscular, or intraperitoneal solutions, oral tablets or liquids, topical ointments or creams and transdermal devices (e.g., patches). In one embodiment, the compound is a sterile solution comprising the active ingredient (drug, or compound), and a solvent, such as water, saline, lactated Ringer's solution, or phosphate-buffered saline (PBS). Additional excipients, such as polyethylene glycol, emulsifiers, salts and buffers may be included in the solution.

In one aspect, the dosage form is a transdermal device, or "patch". The general structure of a transdermal patch is broadly known in the pharmaceutical arts. A typical patch includes, without limitation: a delivery reservoir for containing and delivering a drug product to a subject, an occlusive backing to which the reservoir is attached on a proximal side (toward the intended subject's skin) of the backing and extending beyond, typically completely surrounding the reservoir, and an adhesive on the proximal side of the backing, surrounding the reservoir, typically completely, for adhering the patch to the skin of a patient. The reservoir typically comprises a matrix formed from a non-woven (e.g., a gauze) or a hydrogel, such as a polyvinylpyrrolidone (PVP) or polyvinyl acetate (PVA), as are broadly known. The reservoir typically comprises the active ingredient absorbed into or adsorbed onto the reservoir matrix, and skin permeation enhancers. The choice of permeation enhancers typically depends on empirical studies. Certain formulations that may be useful as permeation enhancers include, without limitation: DMSO; 95% Propylene Glycol+5% Linoleic Acid; and 50% EtOH+40% HSO+5% Propylene Glycol+5% Brij30.

Therapeutic/pharmaceutical compositions are prepared in accordance with acceptable pharmaceutical procedures, such as described in *Remington: The Science and Practice of Pharmacy*, 21st edition, ed. Paul Beringer et al., Lippincott, Williams & Wilkins, Baltimore, Md. Easton, Pa. (2005) (see, e.g., Chapters 37, 39, 41, 42 and 45 for examples of powder, liquid, parenteral, intravenous and oral solid formulations and methods of making such formulations).

As shown in the examples below, the compositions as described herein exhibit unexpected synergy when combined with other anticancer therapies, such as chemotherapeutic or radiation therapies as are known in the art. Therefore in one aspect, a method of treatment of a cancer is provided, comprising treating the cancer with a composition comprising a compound comprising a mitochondria-targeting moiety covalently linked to β-lapachone or a β-lapachone derivative according to any aspect described herein and either co-administering a second chemotherapeutic agent, or applying a radiation therapy to the patient while the compound is present in the patient.

As used herein, "chemotherapeutic agents" are compounds or compositions used to treat cancer, including, for example and without limitation: abiraterone acetate, altretamine, amsacrine, anhydro vinblastine, auristatin, bafetinib, bexarotene, bicalutamide, BMS 184476, 2,3,4,5,6-pentafluoro-N-(3-fluoro-4-methoxyphenyl)benzene sulfonamide, bleomycin, bosutinib, busulfan, cachectin, cemadotin, chlorambucil, cyclophosphamide, 3',4'-didehydro-4'-deoxy-8'-norvin-caleukoblastine, docetaxol, doxetaxel, carboplatin, carmustine (BCNU), chlorambucil, cisplatin, cryptophycin, cyclophosphamide, cytarabine, dacarbazine (DTIC), dactinomycin, daunorubicin, decitabine dolastatin, doxorubicin (adriamycin), etoposide, etoposide phosphate, 5-fluorouracil, finasteride, flutamide, hydroxyurea, hydroxyurea-taxanes, ifosfamide, imatinib, irinotecan, liarozole, lonidamine, lomustine (CCNU), MDV3100, mechlorethamine (nitrogen mustard), melphalan, mitoxantrone, mivobulin isethionate, rhizoxin, sertenef, streptozocin, mitomycin, methotrexate, nilotinib, nilutamide, onapristone, oxaliplatin, paclitaxel, ponatinib, prednimustine, procarbazine, RPRI 09881, stramustine phosphate, tamoxifen, tasonermin, taxol, teniposide, topotecan, tretinoin, vinblastine, vincristine, vindesine sulfate, and vinflunine, and pharmaceutically acceptable salts thereof.

EXAMPLES

Example 1—Synthesis of XJB-Conjugated β-Lapachone

Figure 2:
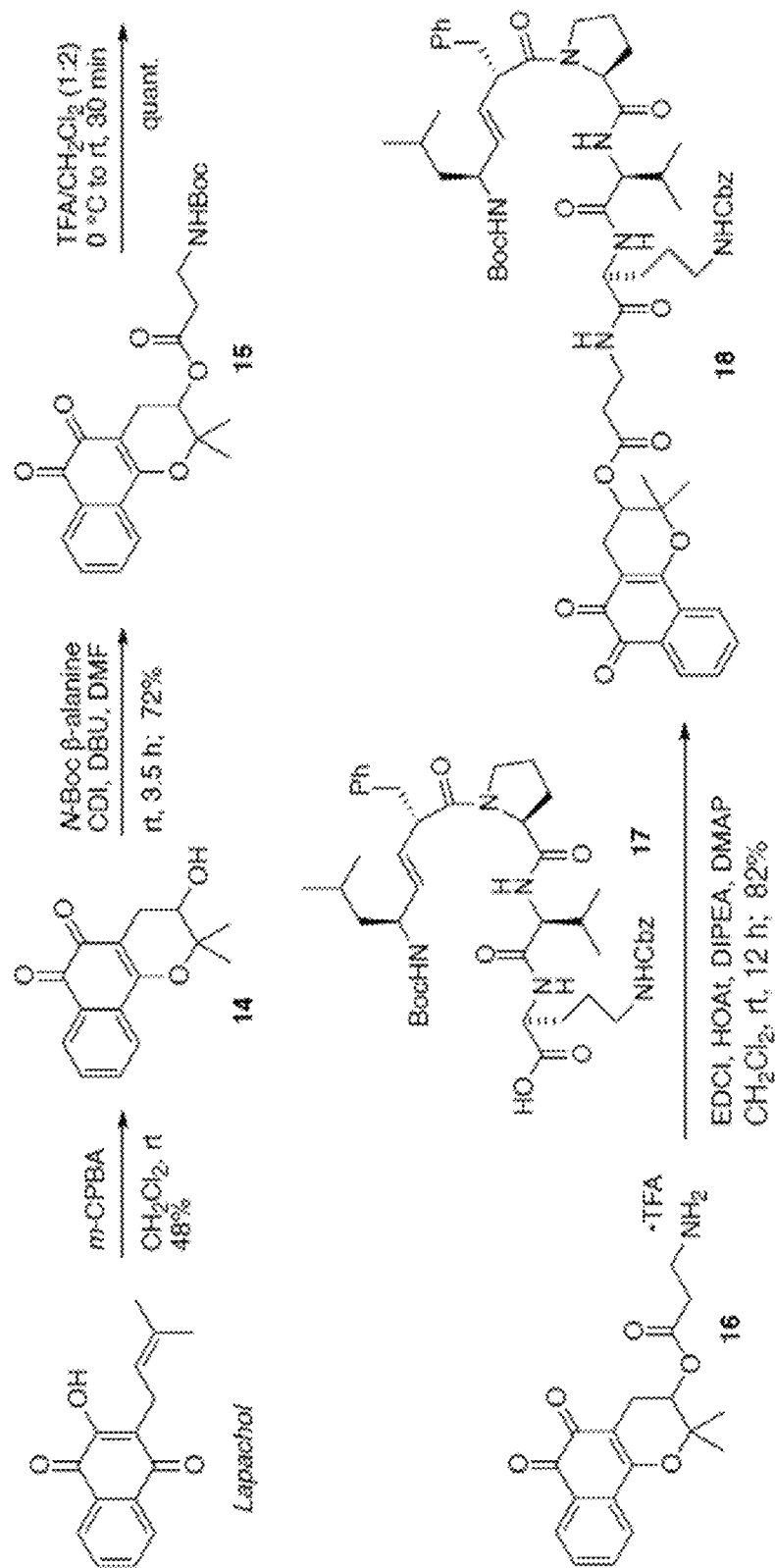
FIG. 2 shows synthesis of a mitochondrial targeted β-lapachone conjugate according to one aspect of the present invention.

For the synthesis of the XJB-conjugated β-lapachone (FIG. 2, Scheme 1), 3-hydroxy β-lapachone (14) was prepared from commercially available lapachol by epoxidation and intramolecular ring opening using meta-chloroperoxybenzoic acid (m-CPBA). The secondary alcohol in 14 was acylated in 72% yield with the N-Boc β-alanine spacer group in the presence of 1,1'-carbonyldiimidazole (CDI) and DBU in DMF. Cleavage of the Boc group in the resulting ester 15 with TFA in $CH_2C_{12}$ afford amine 16 in quantitative yield. The XJB-derived Boc-Leu-$^D$Phe-Pro-Val-Orn(Cbz)-OH targeting sequence 17 was coupled to the amine 16 by EDCI in the presence of HOAt, Hunig's base (DIPEA) and DMAP to afford the desired XJB β-lapachone conjugate 18 in 82% yield.

General. All reactions were performed under $N_2$ atmosphere and all glassware was flame dried in an oven at 150° C. prior to use. $CH_2Cl_2$ was purified using an alumina column filtration system. All other materials were obtained from commercial sources and used as received.

Reactions were monitored by TLC analysis (EM Science pre-coated silica gel 60 $F_{25}4$ plates, 250 m layer thickness) and visualization was accomplished with a 254 nm UV light and by staining with a PMA solution (5 g of phosphomolybdic acid in 100 mL of 95% EtOH), p-anisaldehyde solution (2.5 mL of p-anisaldehyde, 2 mL of AcOH, and 3.5 mL of conc. $H_2SO_4$ in 100 mL of 95% EtOH) or a $KMnO_4$ solution (1.5 g of $KMnO_4$ and 1.5 g of $K_2CO_3$ in 100 mL of a 0.1% NaOH solution). Flash chromatography on $SiO_2$ (SiliaFlash® F60, Silicycle) was used to purify the crude reaction mixtures. Melting points (uncorrected) were determined using a Mel-Temp instrument with a fiber-optic temperature probe. Infrared spectra were obtained on an Identity IR-ATR spectrometer. $^1$H NMR, $^{13}$C NMR, and variable temperature NMR spectra were recorded on a Bruker Avance 400/100 MHz instruments and the $^{13}$C NMR spectrum for compound 18 (XJB-lapachone) was obtained using a Bruker Avance III 700 MHz instruments equipped with a 1.7 mm microprobe. Chemical shifts were reported in parts per million with the residual solvent peak used as an internal standard. $^1$H NMR spectra are tabulated as follows: chemical shift, multiplicity (s=singlet, d=doublet, t=triplet, q=quartet, dd=doublet of doublet, td=triplet of doublet, dt=doublet of triplet, m=multiplet, br=broad, app=apparent), coupling constant(s) and number of protons. All 1D NMR spectra were processed using Bruker Topspin NMR. Final products were >95% purity as analyzed by reverse-phase HPLC (Alltech Prevail C-18, 100×4.6 mm, 1 mL/min, $CH_3CN$, $H_2O$ and 0.1% TFA) with UV (210, 220 and 254 nm), ELS (nebulizer 45° C., evaporator 45° C., $N_2$ flow 1.25 SLM), and MS detection using a Thermo Scientific Exactive Orbitrap LC-MS (ESI positive).

2,2-dimethyl-5,6-dioxo-3,4,5,6-tetrahydro-2H-benzo[h]chromen-3-yl 3-((tert-butoxy carbonyl)amino)propanoate (15) (Sun, J. S.; et al. A preparative synthesis of lapachol and related naphthoquinones. Tetrahedron Lett. 1998 39(45): 8221-8224).

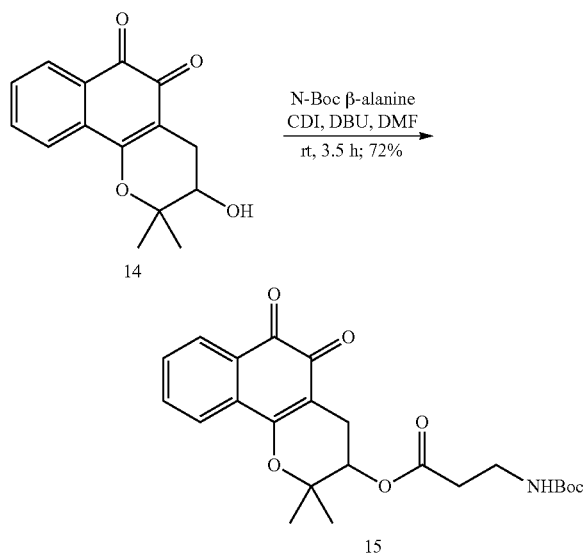

To a solution of N-Boc β-alanine (77.0 mg, 0.40 mmol) in DMF (1.00 mL) was added 1,1'-carbonyldiimidazole (CDI, 67.0 mg, 0.40 mmol) at room temperature. The mixture was stirred for 30 min and treated with alcohol 14 (Salas, C, et al. Trypanosoma cruzi: Activities of lapachol and α- and β-lapachone derivatives against epimastigote and trypomastigote forms, Bioorg. Med. Chem. 2008 16(2):668-674) (70.0 mg, 0.27 mmol) and DBU (54.0 μL, 0.35 mmol). The solution ure was stirred for an additional 3 h, poured into water, and extracted with $CH_2Cl_2$. The combined organic layers were dried ($MgSO_4$) and concentrated. The crude residue was purified by chromatography on $SiO_2$ (Hexanes/EtOAc, 2:1) to give ester 15 (83.3 mg, 72%) as a yellow oil: $^1$H NMR (400 MHz, $CDCl_3$) δ 8.09 (dd, J=7.6, 1.2 Hz, 1H), 7.84 (br d, J=7.6 Hz, 1H), 7.68 (td, J=7.7, 1.5 Hz, 1H), 7.55 (td, J=7.5, 0.9 Hz, 1H), 5.15 (t, J=4.6 Hz, 1H), 4.93 (br s, NH), 3.41-3.35 (m, 2H), 2.84 (dd, J=18.2, 5.0 Hz, 1H), 2.68 (dd, J=18.4, 4.4 Hz, 1H), 2.62-2.48 (m, 2H), 1.48 (s, 3H), 1.44 (s, 3H), 1.42 (s, 9H); $^{13}$C NMR (100 MHz, $CDCl_3$) δ 179.3, 178.5, 171.5, 161.1, 155.7, 134.9, 131.9, 131.1, 130.1, 128.9, 124.3, 109.9, 79.6, 69.4, 34.6, 28.3, 24.9, 23.2, 22.7; IR ($CH_2Cl_2$) 3340, 2975, 2932, 1737, 1705, 1605, 1506, 1390, 1247, 1159, 1133, 727 cm$^{-1}$; HRMS (ESI) calcd for $C_{23}H_{27}O_7NNa$ [M+Na]+452.1680, found 452.1677.

2,2-Dimethyl-5,6-dioxo-3,4,5,6-tetrahydro-2H-benzo[h]chromen-3-yl 3-aminopropanoate (16).

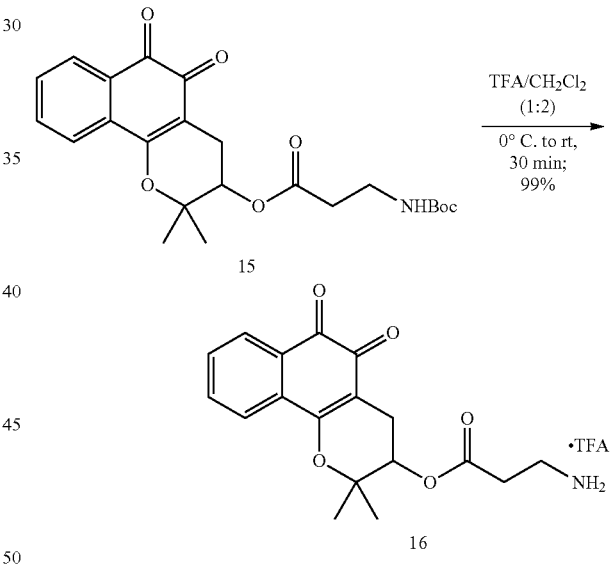

To a solution of N-Boc-protected ester 15 (80.0 mg, 0.19 mmol) in $CH_2Cl_2$ (2.00 mL) was added TFA (1.00 mL) at 0° C. The reaction mixture was stirred at room temperature for 30 min and concentrated under reduced pressure to provide amine 16 (82.0 mg, 99%) as a brick-red solid: Mp 55-60° C.; $^1$H NMR (400 MHz, $D_2O$) δ 7.99 (dd, J=7.8, 1.0 Hz, 1H), 7.94 (dd, J=7.6, 0.8 Hz, 1H), 7.77 (td, J=7.7, 1.5 Hz, 1H), 7.62 (td, J=7.6, 1.2 Hz, 1H), 5.29 (dd, J=4.6, 4.5 Hz, 1H), 3.28 (t, J=6.6 Hz, 2H), 2.93-2.76 (m, 3H), 2.69 (dd, J=18.0, 3.2 Hz, 1H), 1.56 (s, 3H), 1.47 (s, 3H); $^{13}$C NMR (100 MHz, $D_2O$) δ 180.7, 179.8, 171.5, 164.0, 135.7, 131.6, 131.5, 129.4, 128.4, 124.7, 117.7, 114.8, 109.2, 80.7, 70.6, 34.7, 30.9, 23.5, 22.5, 21.8; IR ($CH_2Cl_2$) 3098, 2986, 1735, 1672, 1651, 1601, 1398, 1323, 1197, 1174, 1129, 721; HRMS (ESI) calcd for $C_{18}H_{20}O_5N$ [M+H]+ 330.1336, found 330.1335.

2,2-Dimethyl-5,6-dioxo-3,4,5,6-tetrahydro-2H-benzo[h]chromen-3-yl 3-((S)-2-((S)-2-((S)-1-((2S,5S,E)-2-benzyl-5-((tert-butoxycarbonyl)amino)-7-methyloct-3-enoyl)pyrrolidine-2-carboxamido)-3-methylbutanamido)-5-(((benzyloxy)carbonyl)amino)pentanamido) propanoate (18).

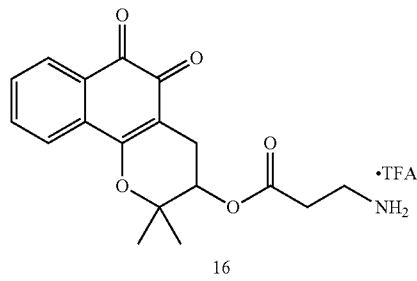
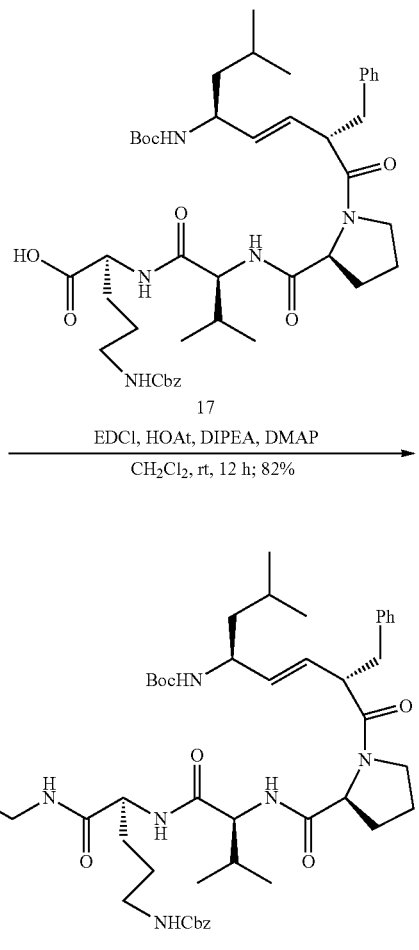

To a mixture of acid 17 (Skoda, E M, et al., Allylic Amines as Key Building Blocks in the Synthesis of (E)-Alkene Peptide Isosteres Org. Process Res. Dev., 2012, 16 (1), pp 26-34) (48.0 mg, 60.0 μmol) and amine 16 (34.0 mg, 77.0 μmol) in CH$_2$Cl$_2$ (2.00 mL) were added 1-ethyl-3-(3-dimethylaminopropyl)carbodiimide (EDCI, 15.0 mg, 77.0 μmol), 1-hydroxy-7-azabenzotriazole (HOAt, 10.7 mg, 77.0 μmol), N,N-diisopropylethylamine (26.0 μL, 150 μmol), and 4-dimethylaminopyridine (0.7 mg, 6.00 μmol). The reaction mixture was stirred at room temperature for 12 h and poured into saturated NH$_4$Cl. The layers were separated, and the aqueous layer was extracted with CH$_2$Cl$_2$. The combined organic layers were dried (MgSO$_4$) and evaporated, and the residue was purified by chromatography on SiO$_2$ (CH$_2$C$_2$/EtOAc, 2:1, followed by 1-5% MeOH/CH$_2$C$_2$) to provide amide 5 (56 mg, 82%) as an orange, foamy solid: Mp 93-100° C.; $^1$H NMR (400 MHz, DMSO-d$_6$, mixture of rotamers, room temperature) δ 8.06-7.88 (m, 3H), 7.81-7.73 (m, 2.5H), 7.66-7.61 (m, 1.5H), 7.36-7.09 (m, 10.2H) 6.98 (d, J=7.2 Hz, 0.8H), 6.78-6.65 (m, 1H), 5.45-5.28 (m, 2H), 5.08-4.92 (m, 3H), 4.56-4.48 (m, 0.4H), 4.40-4.33 (m, 0.6H), 4.25-4.09 (m, 2H), 3.86-3.77 (m, 1H), 3.50-3.43 (m, 2H), 3.26-3.15 (m, 3H), 2.94-2.81 (m, 4H), 2.72 (dd, J=18.2, 4.6 Hz, 1H), 2.67-2.56 (m, 1H), 2.53-2.41 (m, 3H), 2.11-1.54 (m, 8H), 1.42 (s, 3H), 1.38 (s, 3H), 1.35 (s, 9H), 1.23-0.98 (m, 3H), 0.81-0.71 (m, 12H); $^1$H NMR (400 MHz, DMSO-d$_6$, 100° C.) δ 7.95 (d, J=7.2 Hz, 1H), 7.82 (d, J=7.2 Hz, 1H), 7.77 (td, J=7.6, 0.8 Hz, 1H), 7.62 (t, J=7.4 Hz, 1H), 7.56-7.53 (m, 2H), 7.36-7.10 (m, 11H), 6.70 (br s, 1H), 6.08 (br d, J=7.2 Hz, 1H), 5.48 (m, 2H), 5.09 (t, J=4.8 Hz, 1H), 5.02 (s, 2H), 4.41 (m, 1H), 4.27-4.08 (m, 2H), 3.89-3.87 (m, 1H), 3.51-3.45 (m, 2H), 3.39-3.28 (m, 3H), 3.01 (m, 4H), 2.79 (dd, J=18.0, 4.8 Hz, 1H), 2.68 (dd, J=13.8, 7.4 Hz, 1H), 2.57-2.45 (m, 3H), 2.09-1.48 (m, 8H), 1.46 (s, 3H), 1.44 (s, 3H), 1.38 (s, 9H), 1.31-1.10 (m, 3H), 0.87-0.77 (m, 12H); $^{13}$C NMR (175 MHz, DMSO-d$_6$, mixture of rotamers, room temperature) δ 178.8, 178.0, 172.1, 171.6, 171.5, 171.1, 170.7, 159.8, 156.2, 154.9, 154.8, 139.3, 139.2, 137.3, 135.1, 134.6, 134.3, 131.6, 131.1, 130.4, 130.0, 129.2, 128.4, 128.1, 128.0, 127.9, 127.8, 127.3, 126.1, 125.8, 124.8, 123.9, 110.0, 79.5, 77.6, 77.5, 69.1, 65.2, 59.3, 59.0, 58.0, 57.8, 52.3, 50.4, 50.2, 49.0, 48.5, 46.9, 46.7, 44.3, 43.8, 40.0, 38.5, 37.8, 34.7, 33.7, 32.0, 30.5, 30.3, 29.5, 28.3, 26.0, 24.3, 24.1, 23.9, 23.0, 22.6, 22.4, 22.3, 22.1, 19.4, 19.3, 18.4, 18.2, 18.0; IR (CH$_2$Cl$_2$) 3329, 3062, 2975, 1696, 1651, 1606, 1573, 1508, 1392, 1260, 1178, 744, 707 cm$^{-1}$; HRMS (ESI) calcd for $C_{62}H_{81}O_{13}N_6$ [M+H]$^+$ 1117.5856, found 1117.5872.

Example 2

Cell culture: A549 non-small cell lung cancer cells and MDA-MB-231 breast carcinoma cells were obtained from American Type Culture Collection (ATCC). Ovarian cancer cells PEO1 were kindly provided by Dr. Karyn J. Hansen (Magee-Womens Hospital of UPMC). 983B melanoma cells were kindly provided by Dr. Stergios J. Moschos (University of North Carolina). IMR90 normal lung fibroblast cells were kindly provided by Dr. Christopher Bakkenist (University of Pittsburgh Cancer Institute). Cells were cultured in either RPMI 1640 or DMEM media supplemented with 10% heat-inactivated fetal calf serum and 1% penicillin-streptomycin in 5% $CO_2$ at 37° C.

Cell viability and apoptosis assays: Cell viability was determined using a CellTiter-Blue Cell Viability Assay (Promega, Madison, Wis.). The survival fractions were calculated after setting untreated control cells at 100%. An FITC Annexin V Apoptosis Detection Kit (BD PharMingen, San Diego, Calif.) was used to quantify apoptotic cells and necrotic cells, according to the manufacturer's instructions.

Determination of ROS generation: To measure intracellular generation of ROS, cells were incubated with 5 μM DCF-DA (Sigma) for 20 min at 37° C. after drug exposure. To measure mitochondrial generated ROS, cells were incubated with 5 μM of MitoSox (Invitrogen) for 20 min at 37° C. After wash with PBS, cells were trypsinized and suspended in HBSS containing 1% BSA. The fluorescence intensity of DCF and MitoSox were analyzed using an Accuri C6 flow cytometer (BD Accuri Cytometers, Ann Arbor, Mich.).

Extracellular flux (XF) analysis: Oxygen consumption rate (OCR) was measured using a Seahorse XF96 Extracellular Flux Analyzer (Seahorse Bioscience, North Billerica, Mass.), as previously described (Qian W, et al., Alterations in bioenergetics due to changes in mitochondrial DNA copy number. Methods 2010 51:452-457). Briefly, A549 cells were plated in a 6-well plate and treated with compounds for 16 h. After treatment, cells were trypsinized, counted, and plated at 40,000 cells per well in a XF96 microplate using Cell-Tak cell adhesive. OCR measurements were then performed using a XF96 analyzer.

Microscopy: For vacuole imaging, A549 cells were plated in 12-well plate, treated with compounds and the phase contrast images were captured using a Nikon Eclipse TS100 inverted microscope. For transmission electron microscopy analysis, A549 cells cultured in 6-well plate were fixed with 2.5% glutaraldehyde (Sigma-Aldrich) in PBS for 1 h at room temperature, and post-fixed for 1 h at 4° C. in 1% $OsO_4$ with 1% $K_3Fe(CN)_6$. After dehydration and embedding, ultrathin (70 nm) sections were cut and mounted onto copper grids. Sections were stained with 2% uranyl acetate followed by 1% lead citrate, and imaged using a JEOL JEM 1011 transmission electron microscope (Peabody, Mass.) at 80 kV.

Western blot analysis: Western blot was performed. Primary antibody LC3 was obtained from Novus (Littleton, Colo.) and β-actin was purchased from Sigma-Aldrich (St. Louis, Mo.).

Figure 3A:
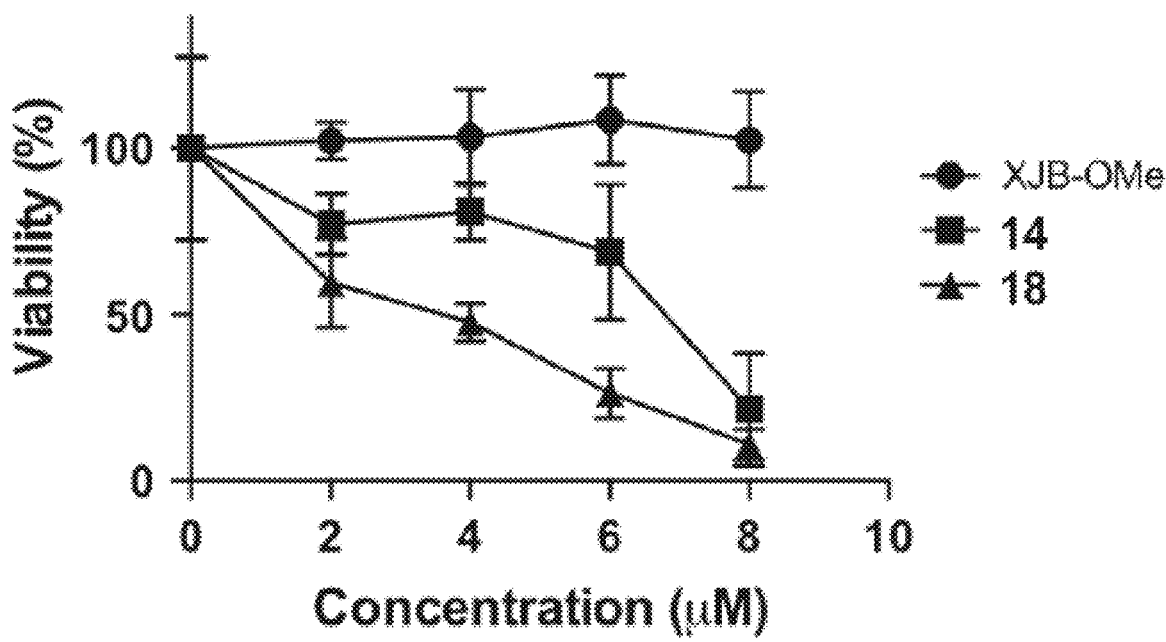
FIG. 3A-3E shows mitochondrial targeted β-lapachone (XJB-lapachone, 18) shows enhanced efficacy and is tumor cell selective. (3A) A549 non-small cell lung cancer cells were treated with XJB-OMe, 3-hydroxy-β-lapachone (14), or XJB-lapachone (18) at indicated concentrations for 24 h. Cell viability was determined by a CellTiter-Blue assay. Data represents the mean±SEM. (3B) PEO1 ovarian cancer cells, MDA-MB-231 breast cancer cells, and 983B melanoma cells were treated with XJB-lapachone (18) at indicated concentrations for 24 h. Cell viability was determined by a CellTiter-Blue assay. Data represents the mean±SEM. (3C) Equal numbers of A549 and IMR90 lung fibroblast cells were treated with 10 μM XJB-lapachone (18) for 4 h. XJB-lapachone was then washed away and cells were incubated in drug free media for 3 days. Cell viability was determined by a CellTiter-Blue assay. (3D) A549 cells were treated with XJB-OMe, 3-hydroxy-β-lapachone (14), or XJB-lapachone (18) at 6 μM concentrations for 20 h. The formation of vacuoles was examined by phase contrast microscopy. Representative images are shown. (3E) A549 cells were treated as described above. Apoptotic and necrotic cell death were determined by Annexin V and PI staining. Representative images are shown.
Figure 3B:
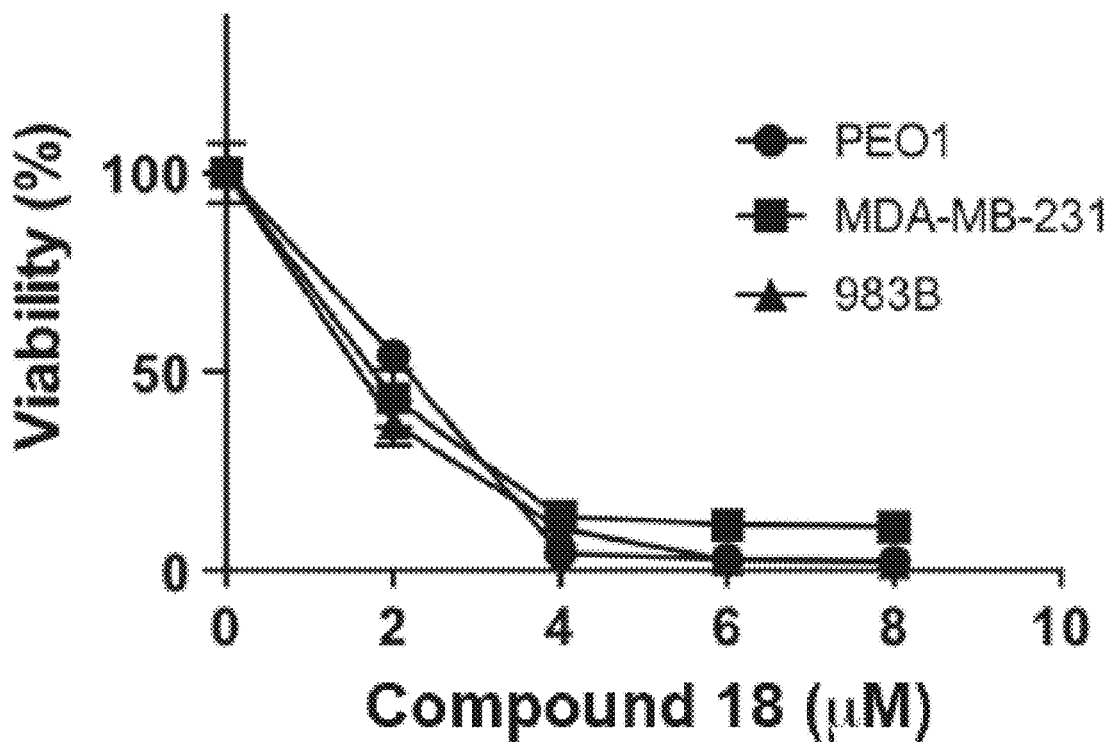
Figure 3C:
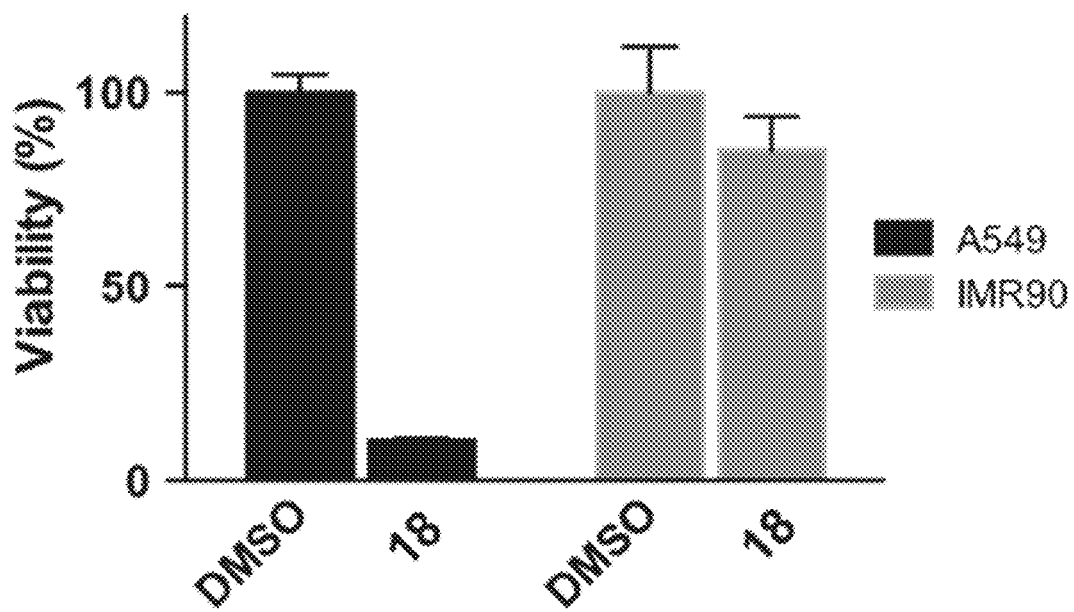
Figure 3D:
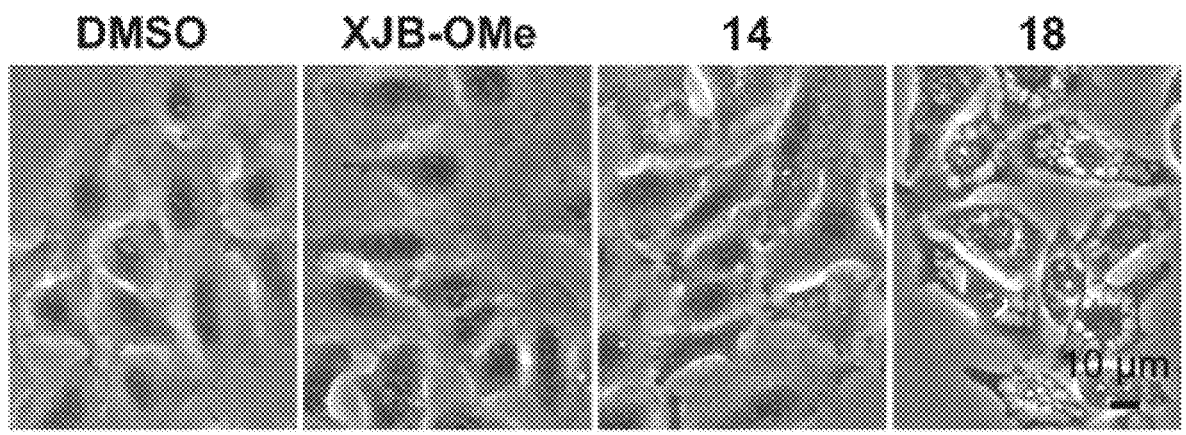
Figure 3E:
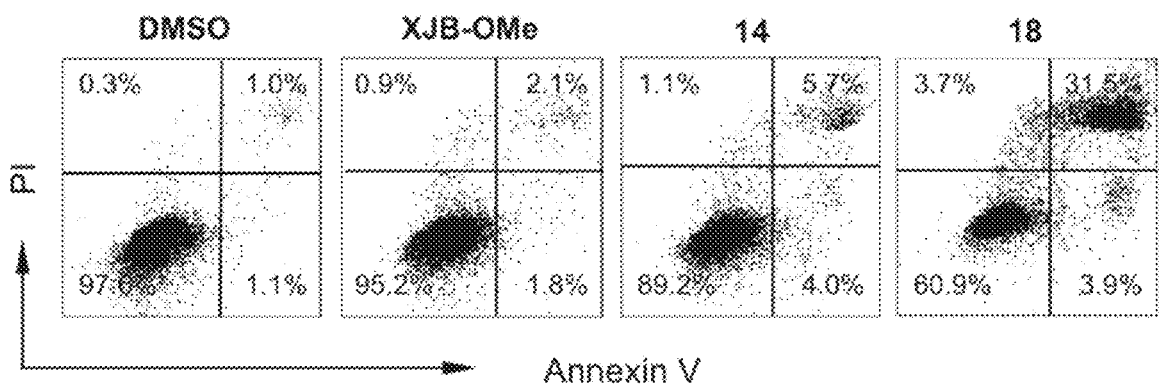

In order to investigate the cellular toxicity of 18 (XJB-lapachone), A549 nonsmall cell lung cancer cells were treated with various concentrations of XJB-lapachone for 24 h, and compared its effect with XJB-OMe (the mitochondrial targeting moiety) and unconjugated 3-hydroxy-β-lapachone (14). A CellTiter-Blue based cell survival assay revealed that XJBLapachone reduced cell viability in a dose dependent manner (FIG. 3A). The cytotoxic effect of XJB-Lapachone is superior compared to unconjugated β-lapachone, while XJB-OMe has no effect on cell survival (FIG. 3A). Furthermore, XJB-lapachone is also effective against other types of tumor cells, including PEO1 ovarian cancer cells, MDA-MB-231 breast cancer cells, and 983B melanoma cells (FIG. 3B). Since MDA-MB-231 breast cancer cells are deficient in NQO1, the high efficacy of XJB-lapachone in this cell type suggests that the effect of the conjugate, mitochondrial targeted XJB-lapachone, is no longer solely dependent on NQO1 activity. β-lapachone is known to have tumor cell-selective toxicity due to higher expression of the enzyme NQO1 in certain tumor cells. Tumor selectivity of β-lapachone, and whether the same is maintained after XJB conjugation, was examined. The cytotoxic effect of XJB-lapachone on A549 lung cancer and non-transformed human lung fibroblast cells IMR90 was determined by a cell growth/death assay. It was found that a four-hour exposure to 10 μM XJB-lapachone significantly reduced the viability of A549 cells, while the toxic effect was less prominent in IMR90 cells, indicating the tumor selectivity of XJB-lapachone (FIG. 3C). Remarkably, in A549 cells extensive vacuolization after XJB-lapachone exposure was observed. In contrast, vacuolization was not detected after treatment with XJB-OMe or 3-hydroxy-β-lapachone (FIG. 3D). β-lapachone has been shown to induce apoptosis or programmed necrosis depending on cell types, and therefore the mechanism of cell death induced by XJB-lapachone was investigated. Through annexin V and PI staining, it was observed that more annexin V positive cells were induced after treatment with XJB-lapachone, compared to unconjugated 3-hydroxy-β-lapachone (FIG. 3E), indicating extensive apoptosis after XJB-lapachone exposure.

Figure 4A:
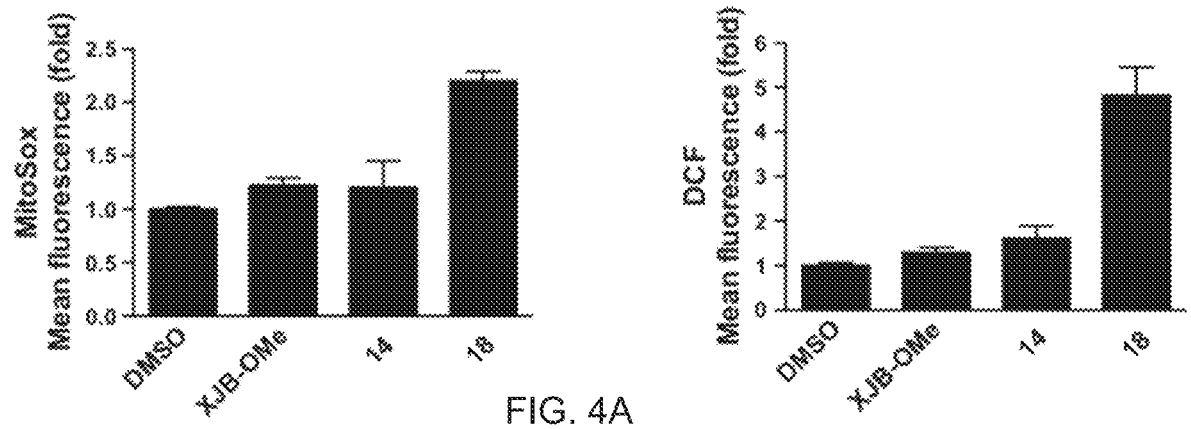
FIG. 4A-4D shows mitochondrial targeted β-lapachone (XJB-lapachone, 18) induces prominent mitochondrial dysfunction. (4A) A549 cells were treated with XJB-OMe, 3-hydroxy-β-lapachone (14), or XJB-lapachone (18) at 6 μM for 16 h. The generation of ROS was determined by staining cells with MitoSox and DCFHDA. The fluorescence intensity was measured by flow cytometry. Data represents the mean±S.D. of triplicates. (4B) A549 cells were treated as described in A, and the oxygen consumption rate was determined by a Seahorse extracellular flux analyzer. These data are the mean±S.D. of six wells, and are representative of three experiments. (4C) A549 cells were treated as described in A, and mitochondria morphology was examined by electron microscopy. Representative images are shown. (4D) A549 cells were treated as described above. The expression of the autophagy marker LC3 was examined by western blot. β-actin was used as a loading control. Representative images are shown.
Figure 4B:
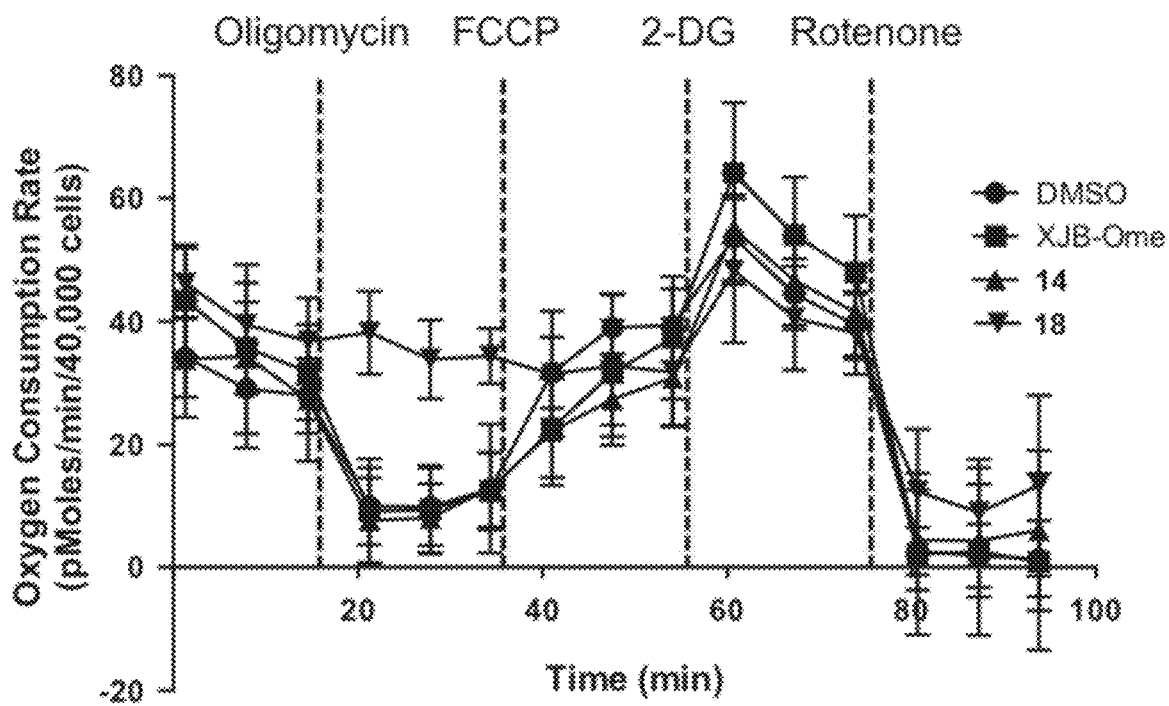
Figure 4C:
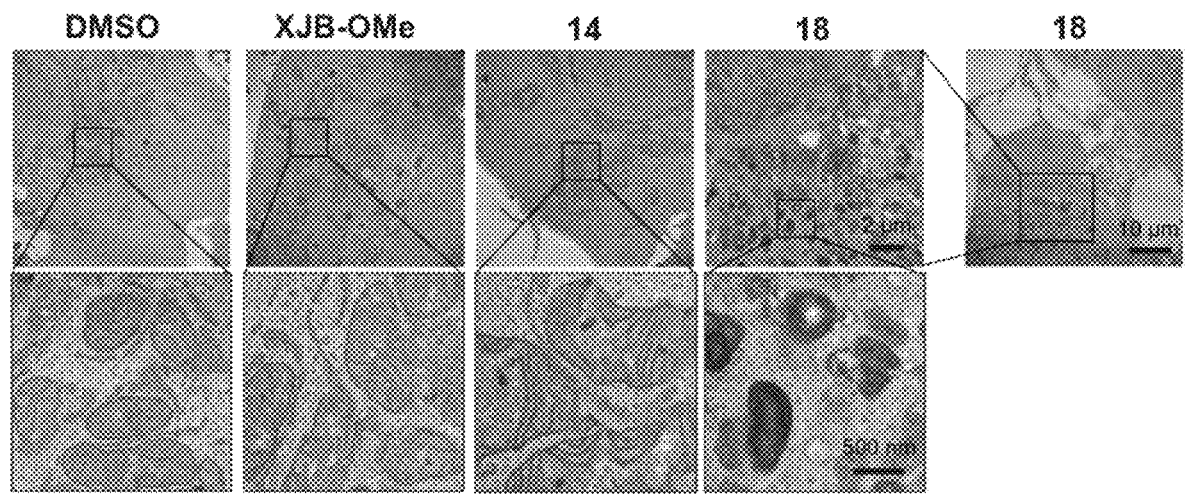
Figure 4D:
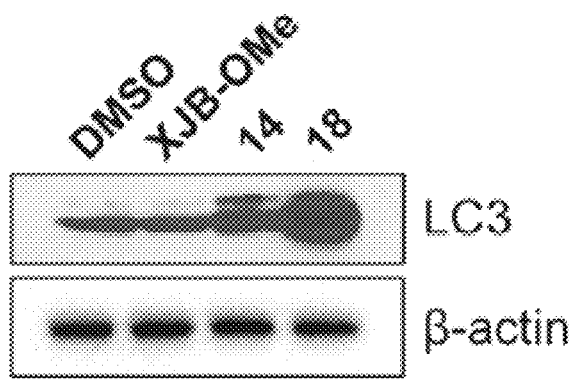

Prior studies have shown that conjugation to the XJB sequence enhances the mitochondrial localization of small heterocyclic payloads by >100-fold. Therefore, the focus was on the effect of XJB-lapachone on mitochondrial function. While β-lapachone is known to promote ROS generation after bio-activation by NQO1 and subsequent NQO1-dependent futile cycling in cytoplasm, XJB-lapachone's activity in MDA-MB-231 cells that lack NQO1 suggests other potential mechanisms. After treating A549 cells with 6 μM XJB-OMe, 3-hydroxy-β-lapachone (14), or XJB-lapachone (18) for 16 h, a dramatic increase of ROS generation was observed after in the presence of XJB-lapachone, as determined by both DCF and the mitochondria-specific superoxide sensor, MitoSox, through flow cytometry analysis. As expected, the effect of the XJB-conjugated, targeted lapachone 18 on ROS generation is stronger than unconjugated 3-hydroxy-β-lapachone (FIG. 4A). Through examining the oxygen consumption of mitochondria, it was further found that following treatment with XJB-lapachone, mitochondrial respiration can no longer be inhibited by oligomycin, which blocks mitochondrial complex V ATP synthase. In contrast, oligomycin was efficient in inhibiting the mitochondrial respiration in cells treated with XJB-OMe or 3-hydroxy-β-lapachone. The absence of response to oligomycin administration indicates a substantial uncoupling effect of the mitochondrial targeted lapachone (FIG. 4B). Electron microscopy analysis further revealed that after treatment with XJB-lapachone in A549 cells onion skin-like structures of mitochondria were observed, and cells developed extensive vacuoles (FIG. 4C). This finding suggests that XJB-lapachone exposure leads to autophagic degradation of mitochondria (mitophagy). Consistent with the morphologic changes of mitochondria during autophagy, an increase in an LC3-II immunoblot signal was observed after XJB-lapachone exposure, in contrast to XJB-OMe and 3-hydroxy-β-lapachone exposure (FIG. 4D), supporting a potential important role of autophagy in XJB-lapachone induced cell death.

The preferential, dramatic effects of XJB-lapachone on mitochondrial function, as compared to unconjugated 14, are conceivably the results of its accumulation in mitochondria leading to the generation of ROS and subsequent ROS-mediated mitochondrial damage, and/or covalent modifications of nucleophilic mitochondrial components. Furthermore, the results in FIG. 2 indicate that XJB-lapachone induces cell death at least in part independent on NQO1, and therefore the mechanism of action of XJB-lapachone will require further follow-up investigations. Since the XJB-lapachone conjugate 18 contains an ortho-quinone/catechol substructure, NQO1-independent mechanisms such as a Cu(II) or Fe(III) chelation may play a significant role in its mitochondrial toxicity. Combined, these data suggest that mitochondrial targeting of β-lapachone results in the activation of unique signaling pathways leading to a yet to be classified type of cell death as highlighted by an extensive formation of vacuoles, in stark contrast to the phenotype of unconjugated β-lapachone.

In summary, a new mitochondrial targeted β-lapachone analog was prepared and its unique effects on cancer cell lines were demonstrated. XJB-lapachone is able to preferentially and efficiently induce mitochondrial ROS generation and subsequent mitochondrial damage, resulting in enhanced cytotoxicity compared to unconjugated β-lapachone. Due to the altered mitochondrial function and ROS metabolism in cancer cells compared to normal cells, mitochondrial targeted lapachone may yield a higher tumor selectivity than unconjugated lapachone. The remarkable cellular vacuolization is a striking result observed upon treatment of A549 cells with XJB-lapachone (18), but not with XJB-OMe or the control 3-hydroxy-β-lapachone (14).

Taken together, these results support the selection of mitochondria as cancer targets. While many tumors have the capacity to produce a large percentage of their ATP through glycolysis, i.e. the Warburg effect, it is clear that tumor cells are metabolically flexible and can adapt to the harsh tumor environment by altering their carbon sources to provide energy and key metabolic intermediates. In addition, oncogene overexpression, such as Myc, while increasing glycolysis can also increase mitochondrial biogenesis. Thus, mitochondrial function is a vital factor in tumor cells. In addition, cancer cells have a higher ROS load and are likely saturating their scavenging mechanisms. Their ability to respond to additional mitochondrial stress factors is reduced. Furthermore, many apoptosis-avoiding mutations are upstream from mitochondria, thus retaining cellular susceptibility to mitochondria-triggered death signals. Ongoing investigations on the mechanism of XJB-lapachone generation of ROS and its associated cell death pathway will provide a basis for exploring the therapeutic potential of this novel agent and establish a platform for the design of next generation mitochondrial targeted ROS generators for cancer therapy. Mechanism-based combination designs such as simultaneous inhibition of several antioxidant systems will likely further enhance the efficacy of mitochondrial targeted lapachone.

Further, neurodegenerative diseases are conditions in which nerve cells from the brain and spinal cord are lost. This leads to either functional loss (ataxia), or sensory dysfunction (dementia). Mitochondrial dysfunction, excitotoxicity and apoptosis are considered to be a pathological cause for aging and neurodegenerative diseases such as Parkinson's disease (PD), Alzheimer's disease (AD), Multiple Sclerosis (MS) and amyotrophic lateral sclerosis (ALS). Although neurodegeneration is speculated to involve a number of factors, including environmental and genetic predisposition, but oxidative stress and free radical generation e.g., catalyzed by redox metals, have been shown to play pivotal role in regulating redox reactions in vivo, contributing RNS (reactive nitrogen species, such as nitric oxide (NO)) and ROS (reactive oxygen species, such as hydroxyl (OH—) and superoxide ($O_2^-$)), which are considered to be significant factors in neurodegeneration (See, e.g., Uttara, B, et al., Oxidative Stress and Neurodegenerative Diseases: A Review of Upstream and Downstream Antioxidant Therapeutic Options, Curr Neuropharmacol. 2009 March; 7(1): 65-74 and Chen, X, et al., Oxidative stress in neurodegenerative diseases, Neural Regen Res. 2012 Feb. 15; 7(5): 376-385; Gruber et al., Mitochondria-targeted antioxidants and metabolic modulators as pharmacological interventions to slow ageing. *Biotechnol. Adv.* 2013, 31, 563-592).

Figure 5:
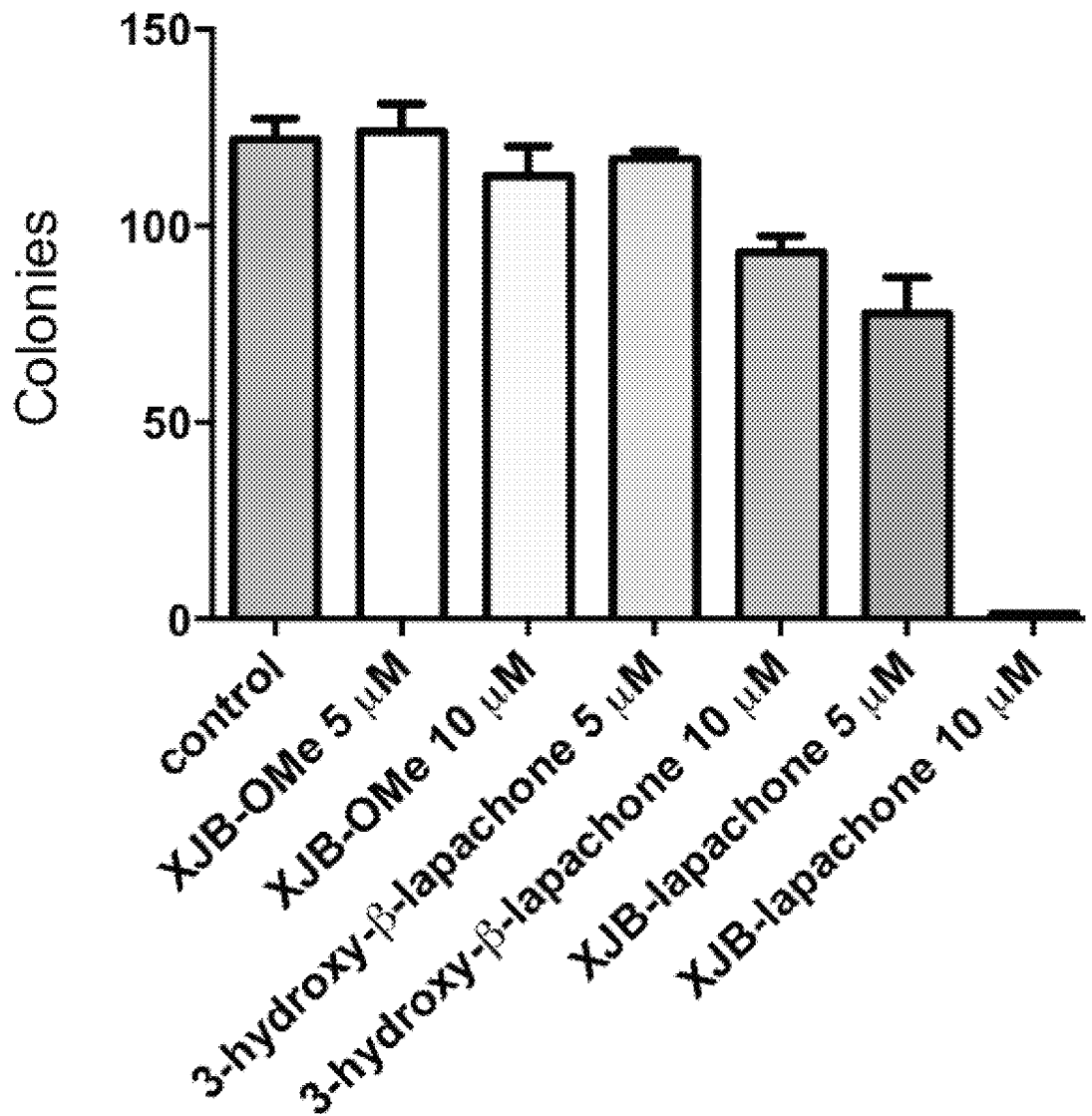
FIG. 5 shows a graph showing that mitochondrial-targeted β-lapachone (XJB-lapachone) has higher treatment efficacy as compared to unconjugated β-lapachone (3-hydroxy-β-lapachone).

Example 3—Mitochondrial-Targeted Beta-Lapachone (XJB-Lapachone) has Higher Treatment Efficacy as Compared to Unconjugated Beta-Lapachone As shown in FIG. 5, A549 non-small cell lung cancer cells were treated with indicated agents for 4 h. Drug efficacy was determined by colony forming capacity using crystal violet 10 days after drug treatment.

Example 4—XJB-Lapachone Induces Mitochondrial ROS Generation in a Dose and Time Dependent Manner and is Independent of NQO1

Figure 6:
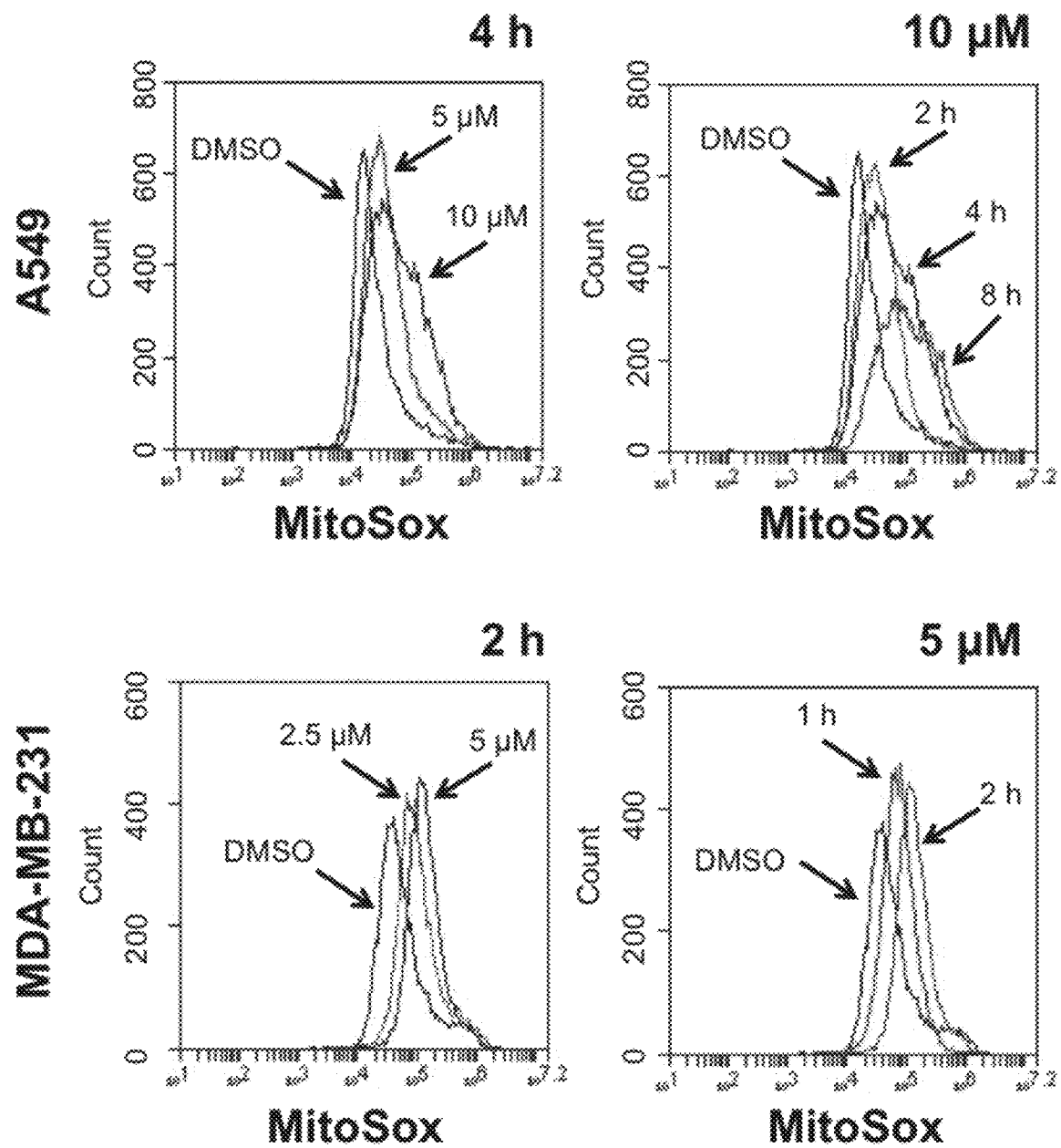
FIG. 6 shows graphs showing that XJB-lapachone induces mitochondrial ROS generation in a dose and time dependent manner and is independent of NQO1.

A549 non-small cell lung cancer cells (high NQO1) and MDA-MB-231 triple negative breast cancer cells (NQO1 deficient) were treated as indicated in FIG. 6. Mitochondrial ROS generation was determined by MitoSox followed by flow cytometry, essentially as described above.

Figure 7:
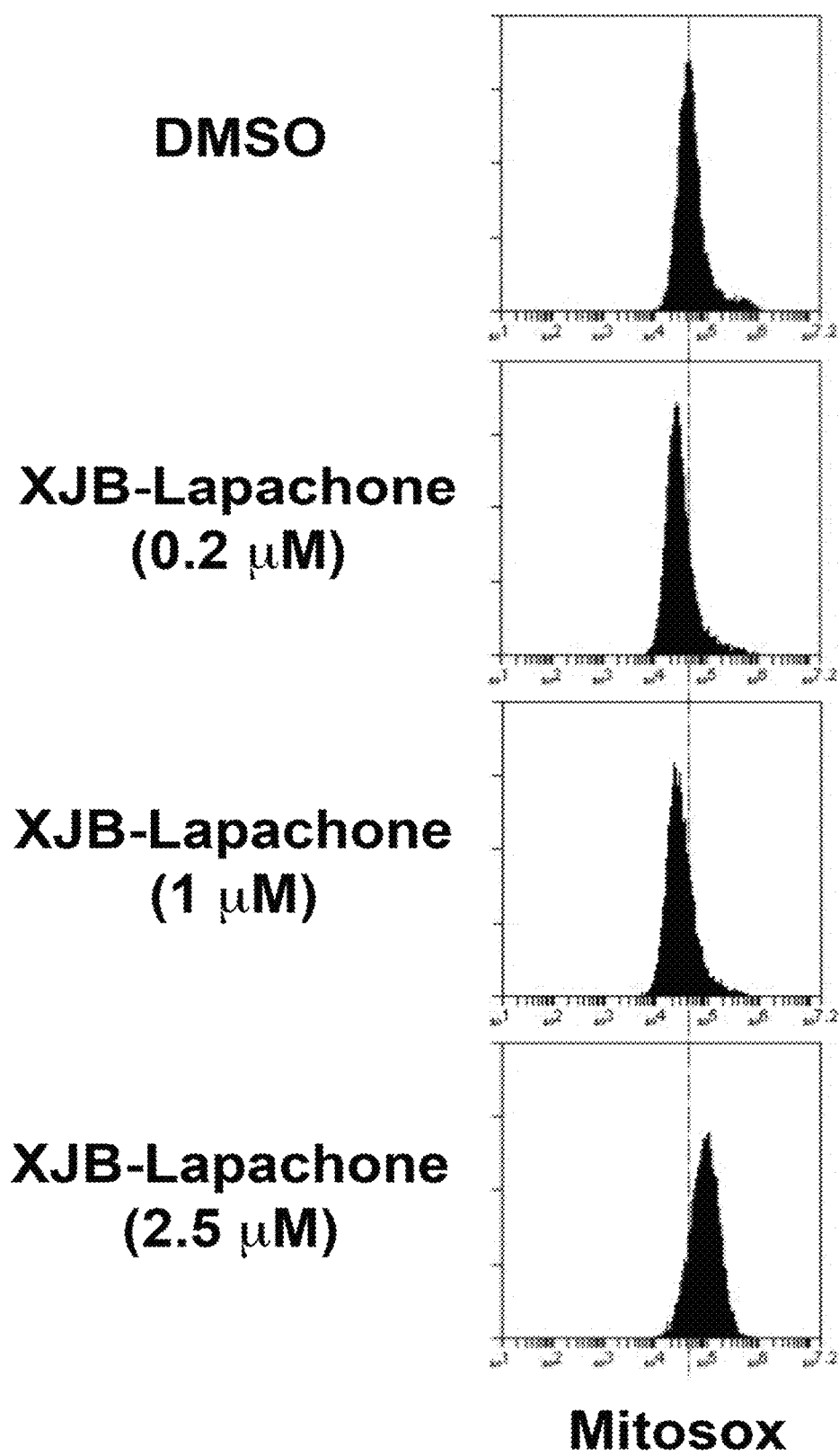
FIG. 7 shows graphs showing that low concentration of XJB-lapachone reduces mitochondrial ROS levels, while high concentration increases mitochondrial ROS.

Example 5—Low Concentration of XJB-Lapachone Reduces Mitochondrial ROS Levels, while High Concentration Increases Mitochondrial ROS MDA-MB-231 triple negative breast cancer cells (NQO1 deficient) were treated as indicated in FIG. 3 for 2 h. Mitochondrial ROS generation was determined by MitoSox followed by flow cytometry. Left-shift of peak indicates decrease of ROS and right-shift of peak indicates increase of ROS. FIG. 7 indicates that greater concentrations of XJB-lapachone in cancer cells can selectively kill the cancer cells by promoting ROS, while non-enriching cells can be protected through lowering ROS levels.

Figure 8:
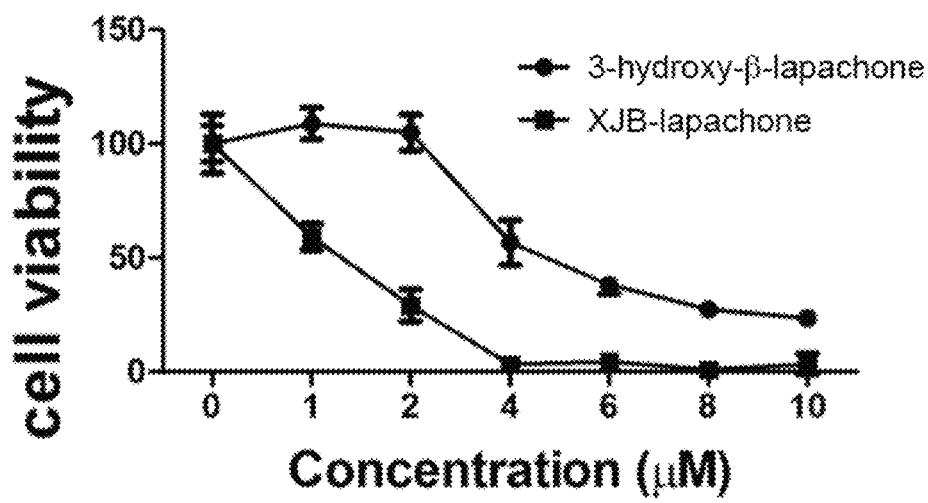
FIG. 8 shows graphs showing that XJB-lapachone but not unconjugated beta-lapachone (3-hydroxy-β-lapachone) is effective in inducing cell death in rho0 cells.
Figure 8:
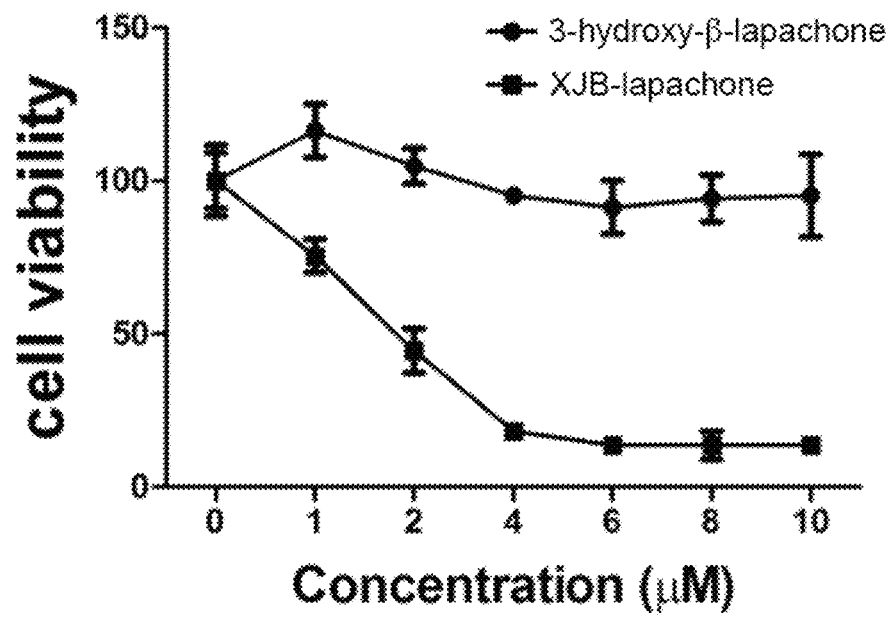

Example 6—XJB-Lapachone but not Unconjugated β-Lapachone is Effective in Inducing Cell Death in rho0 Cells MDA-MB-231 parental and rho0 cells (established by long-term culture of parental MDA-MB-231 cells in the presence of 50 ng/ml ethidium bromide) were treated with increasing concentrations of XJB-lapachone for 24 h. Cell viability was determined by Celltiter-blue. As shown in FIG. 8, XJB-lapachone but not uncojugated β-lapachone (3-hydroxy-β-lapachone) is effective in inducing cell death in rho0 cells, which are depleted of mtDNA and hence resistant to multiple anticancer agents.

Example 7—XJB-Lapachone Induces DNA Damage

Figure 9:
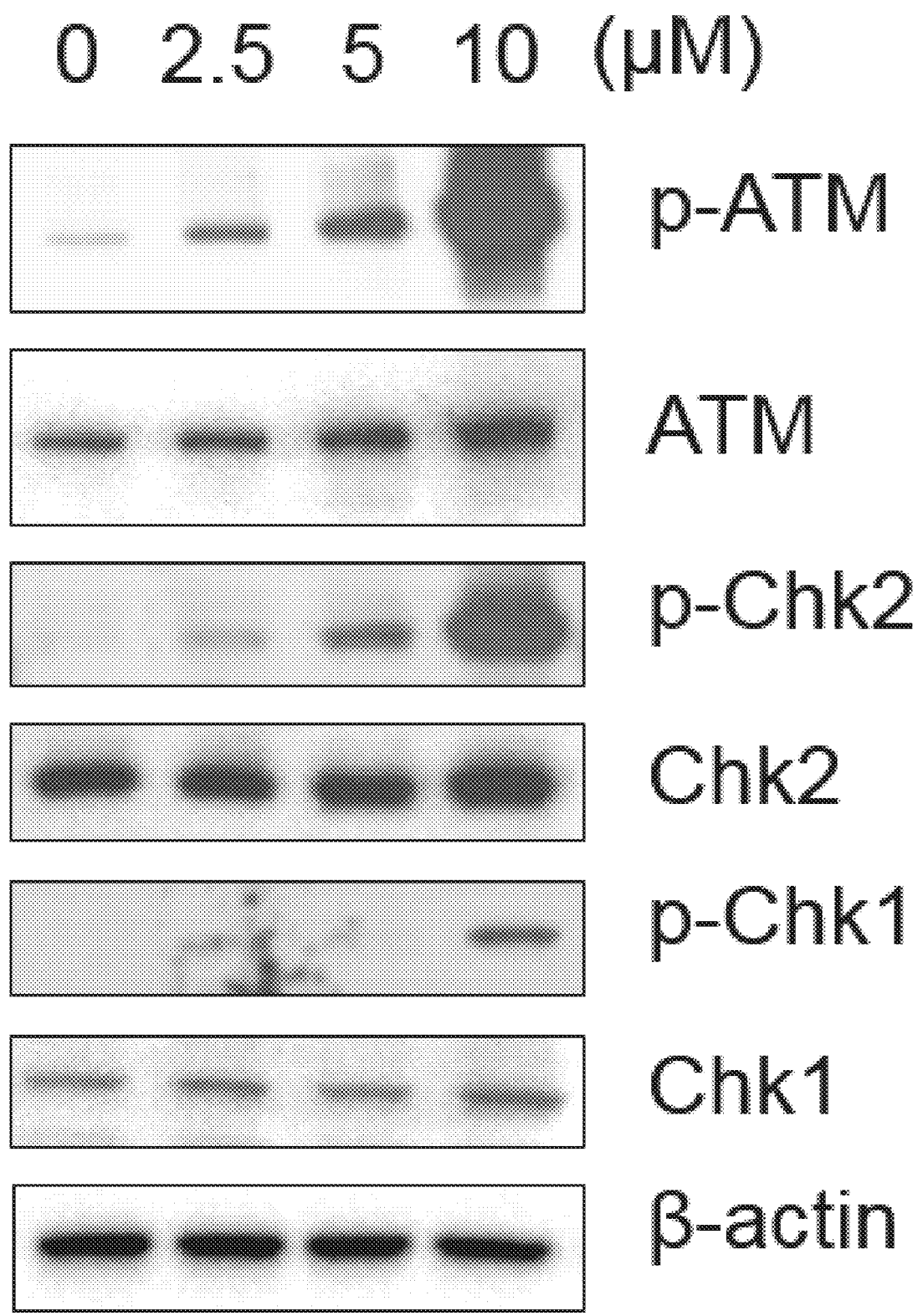
FIG. 9 shows a Western blot showing that XJB-lapachone induces DNA damage.

A549 cells were treated with XJB-lapachone at the concentrations indicated in FIG. 5. Western blot was performed 4 4 after treatment to examine the activation of DNA damage signaling. Antibodies used in the Western Blot were β-actin (AC-15) and ATM (MAT3-4G10/8) (from Sigma); Chk1 (2G1D5), phospho-Chk2 (Thr68) (C13C1), Chk2 (1C12) (from Cell Signaling Technology); phospho-Chk1 (Ser317) (from R&D systems); and phospho-ATM (S1981) (from Epitomics). FIG. 9 shows that XJB-lapachone induces DNA damage.

Figure 10:
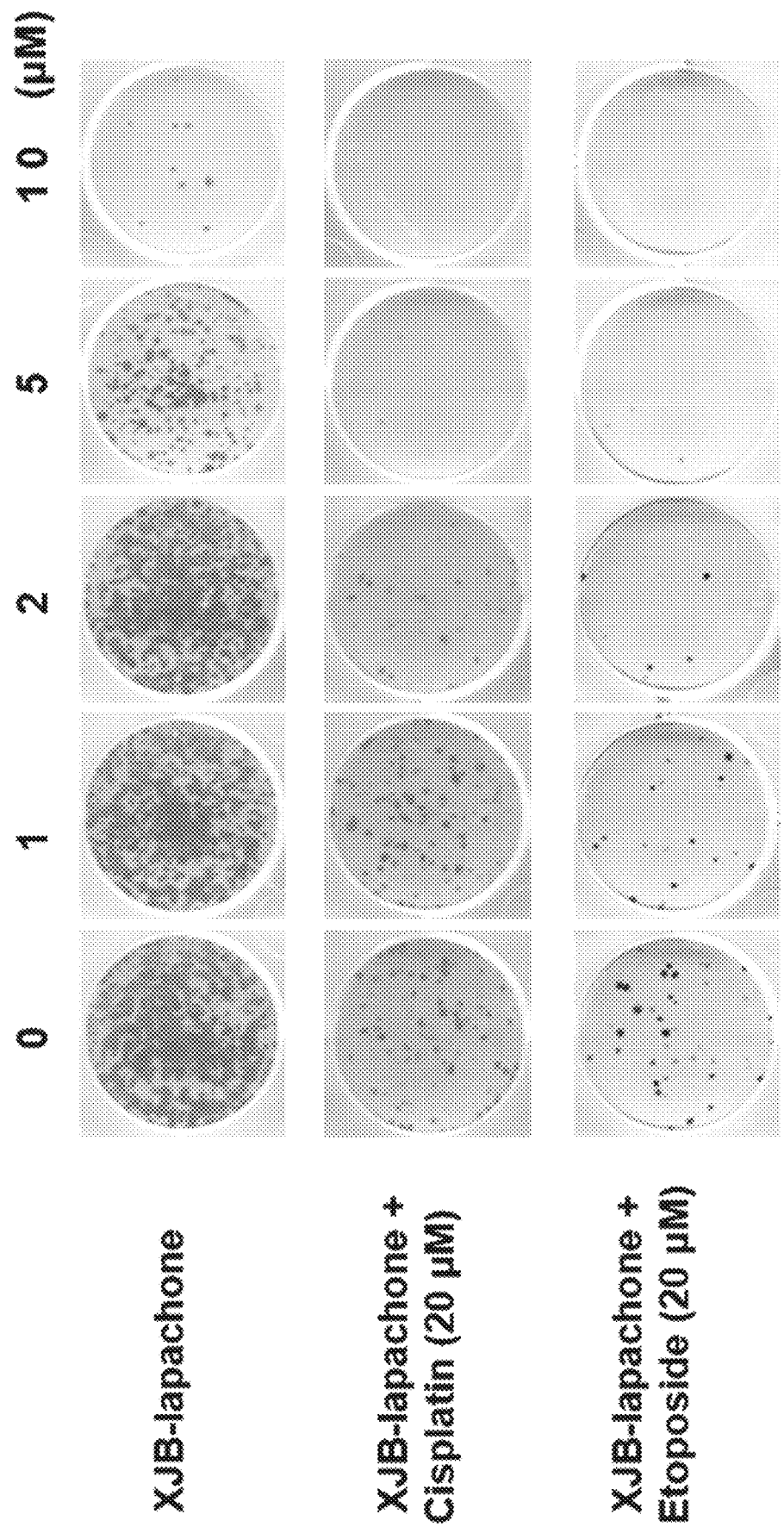
FIG. 10 shows a photograph of A549 cell cultures indicating that XJB-lapachone enhances the effect of DNA-damaging anticancer agents.

Example 8—XJB-Lapachone Enhances the Effect of DNA-Damaging Anticancer Agents A549 non-small cell lung cancer cells were treated with XJB-lapachone alone or combination with cisplatin or etoposide for 4 h at concentrations indicated in FIG. 10. Drug efficacy was determined by colony forming capacity 10 days after drug treatment. As seen in FIG. 10, XJB-lapachone enhances the effect of DNA-damaging anticancer agents.

Example 9—Synergistic Effect of XJB-Lapachone with Ionizing Radiation (IR)

Figure 11:
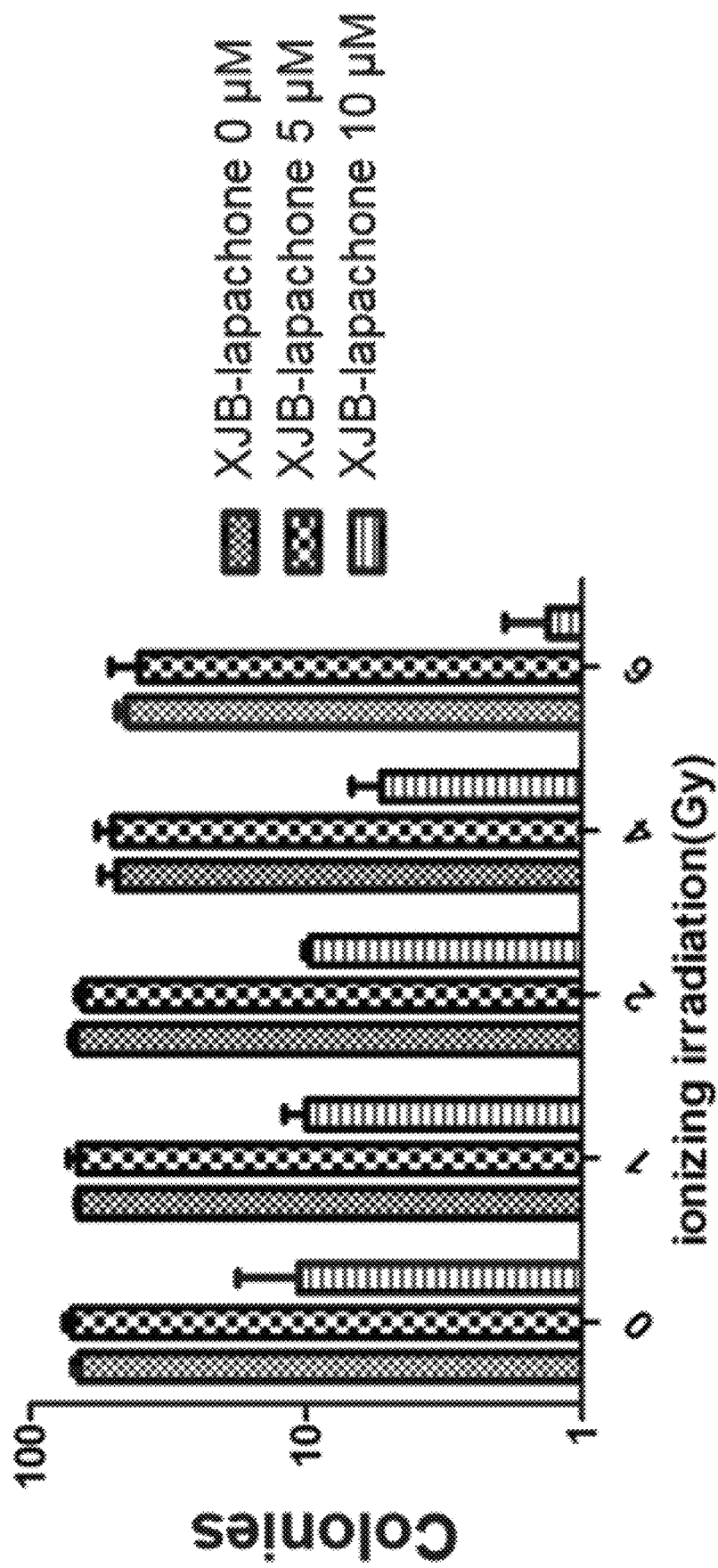
FIG. 11 shows synergistic effects of XJB-lapachone and ionizing radiation on colonies of A549 cells.

A549 cells were treated with XJB-lapachone for 4 h. XJB-lapachone was then washed away before IR exposure (gamma-irradiation with a Shepherd Mark I Model 68 [$^{137}$Cs] irradiator) at 0, 1, 2, 4, and 6 Gy (grays). The number of colonies was counted 10 days after IR exposure (FIG. 11).

Having described this invention above, it will be understood to those of ordinary skill in the art that the same can be performed within a wide and equivalent range of conditions, formulations and other parameters without affecting the scope of the invention or any embodiment thereof. Any document incorporated herein by reference is only done so to the extent of its technical disclosure and to the extent it is consistent with the present document and the disclosure provided herein.

We claim:

1. A compound of formula (I):

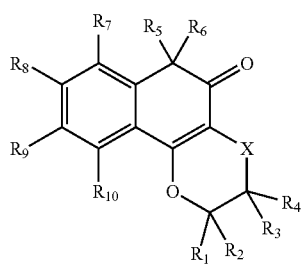

or a pharmaceutically acceptable salt thereof, wherein:

$R_1$ is H, OH, $C_1$-$C_6$ alkyl, $C_2$-$C_6$ alkenyl, $C_1$-$C_6$ alkoxy, $C_1$-$C_6$ alkoxycarbonyl, —$(CH_2)_n$-aryl, —$(CH_2)_n$-heteroaryl, —$OR_a$, alkylamino, dialkylamino, or heterocyclyl;

$R_a$ is H, amido, heterocyclyl, or Si(alkyl)$_3$;

$R_2$ is H, OH, $C_1$-$C_6$ alkyl, $C_2$-$C_6$ alkenyl, $C_1$-$C_6$ alkoxy, —$(CH_2)_n$-aryl, —$(CH_2)_n$heteroaryl, C(O)OH, or C(O)O$C_1$-$C_6$ alkyl;

$R_3$ is H, OH, $C_1$-$C_6$ alkyl, $C_2$-$C_6$ alkenyl, $C_1$-$C_6$ alkoxy, C(O)H, C(O)$C_1$-$C_6$ alkyl, C(O)O$C_1$-$C_6$ alkyl, amino, alkylamino, dialkylamino, —$(CH_2)_n$-aryl, —$(CH_2)_n$heteroaryl, or heterocyclyl;

$R_4$ is H, OH, $C_1$-$C_6$ alkyl, $C_2$-$C_6$ alkenyl, $C_1$-$C_6$ alkoxy, C(O)H, C(O)$C_1$-$C_6$ alkyl, C(O)O$C_1$-$C_6$ alkyl, amino, alkylamino, dialkylamino, —$(CH_2)_n$-aryl, —$(CH_2)_n$heteroaryl, or heterocyclyl;

$R_5$ and $R_6$, together with the carbon atom to which they are attached, are —C(O)—;

$R_7$ is H, halogen, OH, $NO_2$, CN, $C_1$-$C_6$ alkyl, $C_1$-$C_6$ alkoxy, C(O)OH, C(O)O$C_1$-$C_6$ alkyl, C(O)$NH_2$, amino, alkylamino, dialkylamino, aryl, benzyl, heteroaryl, or heterocyclyl;

$R_8$ is H, halogen, OH, $NO_2$, CN, $C_1$-$C_6$ alkyl, $C_1$-$C_6$ alkoxy, C(O)OH, C(O)O$C_1$-$C_6$ alkyl, C(O)$NH_2$, amino, alkylamino, dialkylamino, aryl, benzyl, heteroaryl, or heterocyclyl;

$R_9$ is H, halogen, OH, $NO_2$, CN, $C_1$-$C_6$ alkyl, $C_1$-$C_6$ alkoxy, C(O)OH, C(O)O$C_1$-$C_6$ alkyl, C(O)$NH_2$, amino, alkylamino, dialkylamino, aryl, benzyl, heteroaryl, or heterocyclyl;

$R_{10}$ is H, halogen, OH, $NO_2$, CN, $C_1$-$C_6$ alkyl, $C_1$-$C_6$ alkoxy, C(O)OH, C(O)O$C_1$-$C_6$ alkyl, C(O)$NH_2$, amino, alkylamino, dialkylamino, aryl, benzyl, heteroaryl, or heterocyclyl;

X is —$CH_2$—; and n is 0, 1, 2, or 3;

with the proviso that covalently bonded to formula (I) at one of $R_1$, $R_2$, $R_3$, or $R_4$ is a mitochondrial targeting group represented by the formula below:

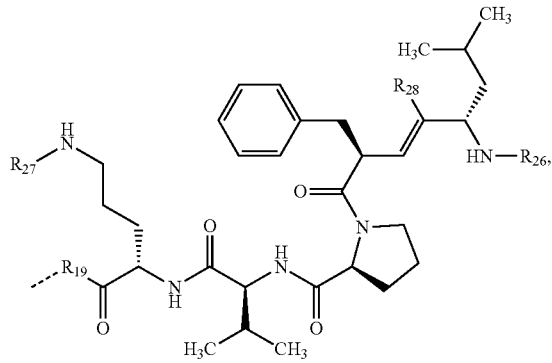

wherein:

$R_{19}$ is —$CH_2$—, —NH—, or —O—;

$R_{26}$ and $R_{27}$ are each independently H or an amine protecting group independently selected from the group consisting of:

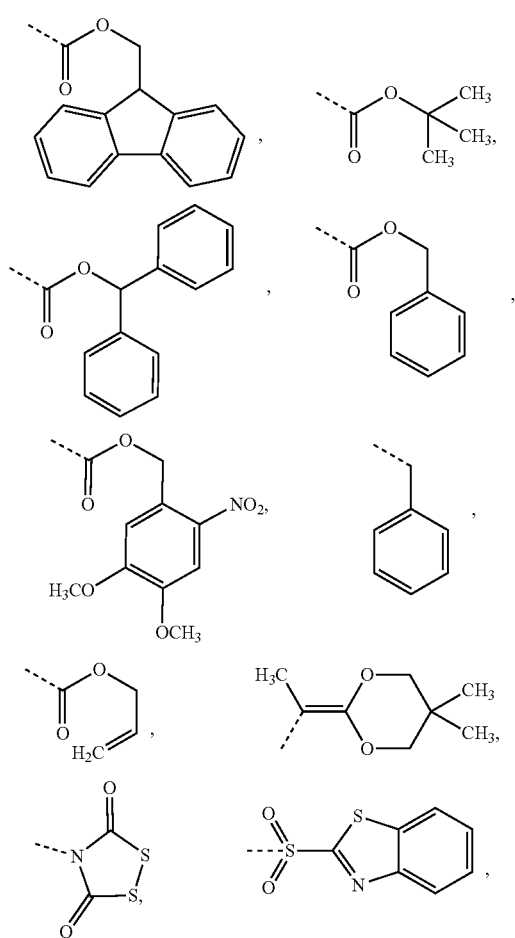
$R_{28}$ is H or $CH_3$.
2. The compound of claim 1, or a pharmaceutically acceptable salt thereof, wherein $R_{26}$ and $R_{27}$ are each independently an amine protecting group independently selected from the group consisting of:
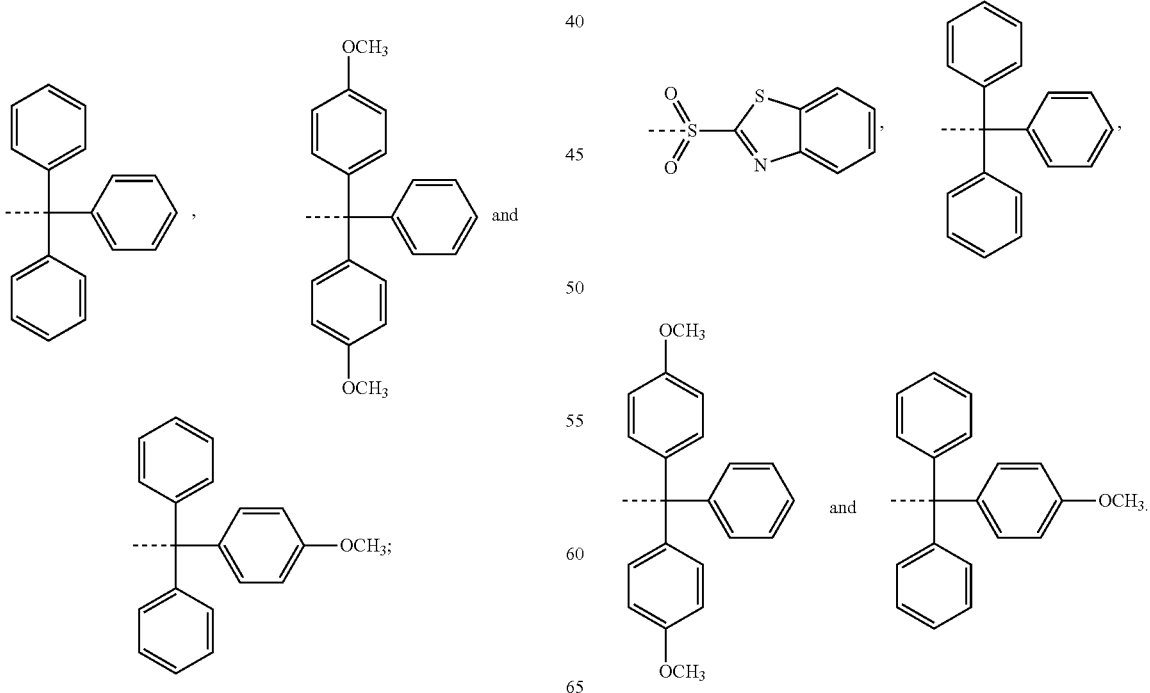

3. The compound of claim 2, or a pharmaceutically acceptable salt thereof, wherein $R_{26}$ and $R_{27}$ are each independently an amine protecting group independently selected from the group consisting of:

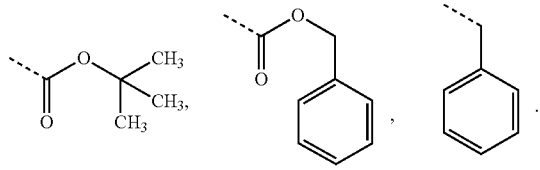

4. The compound of claim 1, or a pharmaceutically acceptable salt thereof, wherein the mitochondrial targeting group is covalently bonded to formula (I) at one of $R_3$ or $R_4$.

5. The compound of claim 4, or a pharmaceutically acceptable salt thereof, wherein:

$R_{26}$ is

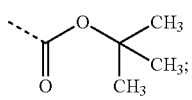

and $R_{27}$ is

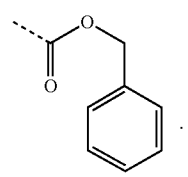

6. The compound of claim 4, or a pharmaceutically acceptable salt thereof, wherein $R_{28}$ is H.

7. The compound of claim 1, wherein the compound has the structure:

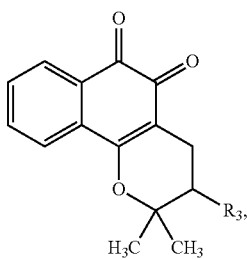

or a pharmaceutically acceptable salt thereof.

8. A pharmaceutical composition comprising a pharmaceutically acceptable carrier and the compound of claim 1, or a pharmaceutically acceptable salt thereof.

9. The pharmaceutical composition of claim 8, wherein the pharmaceutical composition further comprises a chemotherapeutic agent.

10. The pharmaceutical composition of claim 9, wherein the chemotherapeutic agent is selected from the group consisting of abiraterone acetate, altretamine, amsacrine, anhydro vinblastine, auristatin, bafetinib, bexarotene, bicalutamide, 2,3,4,5,6-pentafluoro-N-(3-fluoro-4-methoxyphenyl)benzenesulfonamide, bleomycin, bosutinib, busulfan, cachectin, 3',4'-didehydro-4'-deoxy-8'-norvincaleukoblastine, carboplatin, carmustine, cemadotin, chlorambucil, cisplatin, cryptophycin, cyclophosphamide, cytarabine, dacarbazine, dactinomycin, daunorubicin, decitabine, docetaxol, dolastatin, doxetaxel, doxorubicin, etoposide, etoposide phosphate, 5-fluorouracil, finasteride, flutamide, hydroxyurea, hydroxyurea taxanes, ifosfamide, imatinib, irinotecan, liarozole, lomustine, lonidamine, mechlorethamine, melphalan, methotrexate, mitomycin, mitoxantrone, mivobulin isethionate, nilotinib, nilutamide, onapristone, oxaliplatin, paclitaxel, ponatinib, prednimustine, procarbazine, rhizoxin, sertenef, stramustine phosphate, streptozocin, tamoxifen, tasonermin, taxol, teniposide, topotecan, tretinoin, vinblastine, vincristine, vindesine sulfate, and vinflunine.

11. A method for treating cancer in a patient, comprising administering to a patient in need thereof a therapeutically effective amount of the compound of claim 1, or a pharmaceutically acceptable salt thereof.

12. The method of claim 11, wherein the cancer is breast cancer.

13. The method of claim 11, wherein the cancer is lung cancer.

14. The method of claim 11, wherein the cancer is ovarian cancer.

15. The method of claim 11, wherein the cancer is melanoma.

16. The method of claim 11, wherein the method further comprises administering a chemotherapeutic agent to the patient.

17. The method of claim 16, wherein the chemotherapeutic agent is selected from the group consisting of abiraterone acetate, altretamine, amsacrine, anhydro vinblastine, auristatin, bafetinib, bexarotene, bicalutamide, 2,3,4,5,6-pentafluoro-N-(3-fluoro-4-methoxyphenyl)benzenesulfonamide, bleomycin, bosutinib, busulfan, cachectin, 3',4'-didehydro-4'-deoxy-8'-norvin-caleukoblastine, carboplatin, carmustine, cemadotin, chlorambucil, cisplatin, cryptophycin, cyclophosphamide, cytarabine, dacarbazine, dactinomycin, daunorubicin, decitabine, docetaxol, dolastatin, doxetaxel, doxorubicin, etoposide, etoposide phosphate, 5-fluorouracil, finasteride, flutamide, hydroxyurea, hydroxyurea taxanes, ifosfamide, imatinib, irinotecan, liarozole, lomustine, lonidamine, mechlorethamine, melphalan, methotrexate, mitomycin, mitoxantrone, mivobulin isethionate, nilotinib, nilutamide, onapristone, oxaliplatin, paclitaxel, ponatinib, prednimustine, procarbazine, rhizoxin, sertenef, stramustine phosphate, streptozocin, tamoxifen, tasonermin, taxol, teniposide, topotecan, tretinoin, vinblastine, vincristine, vindesine sulfate, and vinflunine.

18. The method of claim 11, wherein the method further comprises simultaneously administering radiation therapy to the patient while the compound, or a pharmaceutically acceptable salt thereof, is present in the patient.

19. A pharmaceutical composition comprising a pharmaceutically acceptable carrier and a compound having the structure:

37
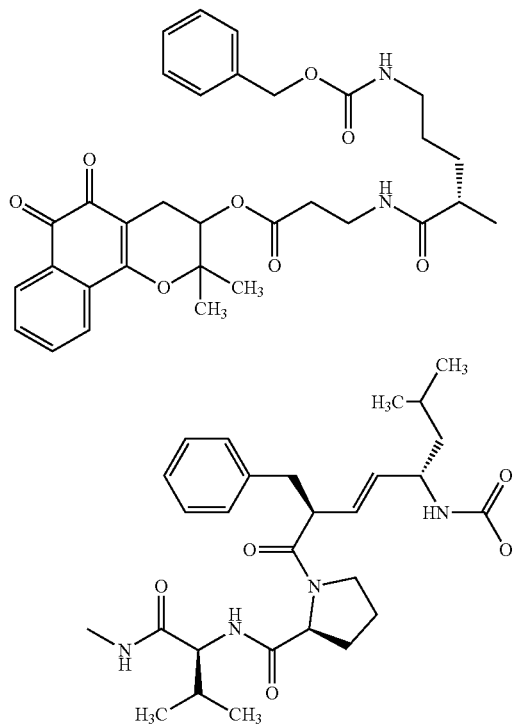
or a pharmaceutically acceptable salt thereof.
20. A method for treating cancer in a patient, comprising administering to a patient in need thereof a therapeutically effective amount of a compound having the structure:
38
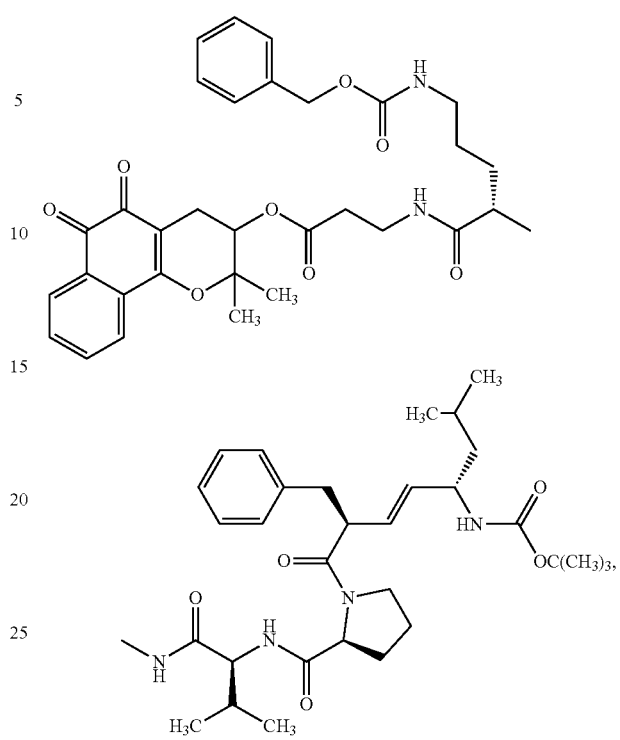
or a pharmaceutically acceptable salt thereof.
* * * * *